United States Patent
Kim et al.

(10) Patent No.: US 10,323,262 B2
(45) Date of Patent: Jun. 18, 2019

(54) MICROORGANISM PRODUCING O-PHOSPHOSERINE AND A METHOD FOR PRODUCING O-PHOSPHOSERINE OR L-CYSTEINE USING THE SAME

(71) Applicant: CJ CHEILJEDANG CORPORATION, Seoul (KR)

(72) Inventors: Sol Kim, Gyeonggi-do (KR); In Hwa Yoo, Incheon (KR); Jin Sook Chang, Seoul (KR); Hye Won Kim, Gyeonggi-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/329,921

(22) PCT Filed: Aug. 10, 2015

(86) PCT No.: PCT/KR2015/008336
§ 371 (c)(1),
(2) Date: Jan. 27, 2017

(87) PCT Pub. No.: WO2016/024771
PCT Pub. Date: Feb. 18, 2016

(65) Prior Publication Data
US 2017/0260556 A1 Sep. 14, 2017

(30) Foreign Application Priority Data

Aug. 12, 2014 (KR) .................. 10-2014-0104670

(51) Int. Cl.
*C12N 1/20* (2006.01)
*C12N 1/14* (2006.01)
(Continued)

(52) U.S. Cl.
CPC ............. *C12P 13/12* (2013.01); *C12N 1/14* (2013.01); *C12N 1/20* (2013.01); *C12N 9/0006* (2013.01);
(Continued)

(58) Field of Classification Search
None
See application file for complete search history.

(56) References Cited

U.S. PATENT DOCUMENTS

| | | | |
|---|---|---|---|
| 2010/0203592 A1* | 8/2010 | Tabata | C07K 14/195 435/71.2 |
| 2011/0111458 A1* | 5/2011 | Masuda | C07K 14/245 435/69.1 |

(Continued)

FOREIGN PATENT DOCUMENTS

| | | |
|---|---|---|
| CN | 102906272 A | 1/2013 |
| EP | 0 885 962 B1 | 4/2005 |

(Continued)

OTHER PUBLICATIONS

UniProt Accession No. M9G2Z2_ECOLX, published May 29, 2013.*

(Continued)

*Primary Examiner* — Richard C Ekstrom
(74) *Attorney, Agent, or Firm* — Cooley LLP

(57) ABSTRACT

The present invention relates to a microorganism, wherein the activity of a polypeptide capable of exporting O-phosphoserine (OPS) is enhanced, and a method of producing O-phosphoserine, cysteine, or a cysteine derivative using the microorganism.

14 Claims, 1 Drawing Sheet

Specification includes a Sequence Listing.

(51) Int. Cl.
    *C12P 13/12*   (2006.01)
    *C12P 13/06*   (2006.01)
    *C12N 9/04*    (2006.01)
    *C12N 9/10*    (2006.01)
    *C12N 9/16*    (2006.01)

(52) U.S. Cl.
    CPC ......... *C12N 9/1085* (2013.01); *C12N 9/1096* (2013.01); *C12N 9/16* (2013.01); *C12P 13/06* (2013.01); *C12Y 101/01095* (2013.01); *C12Y 205/01065* (2013.01); *C12Y 206/01052* (2013.01); *C12Y 301/03003* (2013.01)

(56) References Cited

U.S. PATENT DOCUMENTS

| | | | |
|---|---|---|---|
| 2012/0190081 A1 | 7/2012 | Chang et al. | |
| 2016/0115507 A1* | 4/2016 | Kim | C07K 14/245 435/113 |
| 2016/0130310 A1* | 5/2016 | Kim | C07K 14/245 530/350 |
| 2017/0260556 A1* | 9/2017 | Kim | C12P 13/12 |
| 2017/0342114 A1* | 11/2017 | Kim | C12P 13/005 |
| 2017/0342115 A1* | 11/2017 | Kim | C12P 13/005 |

FOREIGN PATENT DOCUMENTS

| | | |
|---|---|---|
| EP | 0 943 687 B1 | 1/2006 |
| KR | 10-0620092 B | 9/2006 |
| KR | 1020120041115 A | 4/2012 |
| KR | 1020130068135 A | 6/2013 |
| KR | 10-1381048 B | 4/2014 |
| WO | WO-2008/126784 A1 | 10/2008 |

OTHER PUBLICATIONS

Staub et al, "Bacterial glyphosate resistance conferred by overexpression of an *E. coli* membrane efflux transporter," J Ind Microbial Biotechnol (2012) 39:641-647.

Koita et al., "Identification and Analysis of the Putative Pentose Sugar Efflux Transporters in *Escherichia coli*," PLOS ONE (2012) vol. 7, Issue 8, e43700 (pp. 1-10).

Burns et al., "Reconstitution of a new Cysteine biosynthetic pathway in *Mycobacterium tuberculosis*," Journal American Chemical Society 127(33): 11602-11603, Aug. 24, 2005.

Grant et al., "Amino Acid Residue Mutations Uncouple Cooperative Effects in *Escherichia coli* D-3-Phosphoglycerate Dehydrogenase," The Journal of Biological Chemistry 276(21): 17844-17850, May 25, 2001.

Grant et al., "Role of an Interdomain Gly-Gly Sequence at the Regulatory-Substrate Domain Interface in the Regulation of *Escherichia coli*. D-3-Phosphoglycerate Dehydrogenase," Biochemistry 39: 7316-7319, 2000.

Grant et al., "The Contribution of Adjacent Subunits to the Active Sites of D-3-Phosphoglycerate Dehydrogenase," The Journal of Biological Chemistry 274(9): 5357-5361, Feb. 26, 1999.

Mino and Ishikawa, "A novel O-phospho-L-serine sulfhydrylation reaction catalyzed by O-acetylserine sulfhydrylase from Aeropyrum pernix K1," FEBS Letters 551: 133-138, 2003.

NCBI Reference Sequence WP_000130850.1 "Multispecies: putative citrate/iron-citrate/zinc-citrate efflux transporter [Enterobacteriaceae]," Oct. 20, 2014, one page.

NCBI Reference Sequence: WP_001300943.1, "Multispecies: putative arabinose efflux transporter [Enterobacteriaceae]," Oct. 20, 2014, one page.

Peters-Wendisch et al., "Metabolic Engineering of Corynebacterium glutamicum for L-Serine Production," Applied and Environmental Microbiology 71(11):7139-7144, Nov. 2005.

Wada and Takagi, "Metabolic pathways and biotechnological production of L-cysteine," Appl Microbiol Biotechnol 73:48-54, 2006.

Wendisch et al., "Metabolic engineering of *Escherichia coli* and Corynebacterium glutamicum for biotechnological production of organic acids and amino acids," Current Opinion in Microbiology 9:268-274, 2006.

Zahoor et al., "Metabolic Engineering of Corynebacterium glutamicum aimed at alternative carbon sources and new products," Computational and Structural Biotechnology Journal 3(4): Oct. 2012, eleven pages.

Koita and Rao, "Identification and Analysis of the Putative Pentose Sugar Efflux Transporters in *Escherichia coli*," PLoS One 7(8): 1-10, 2012.

* cited by examiner

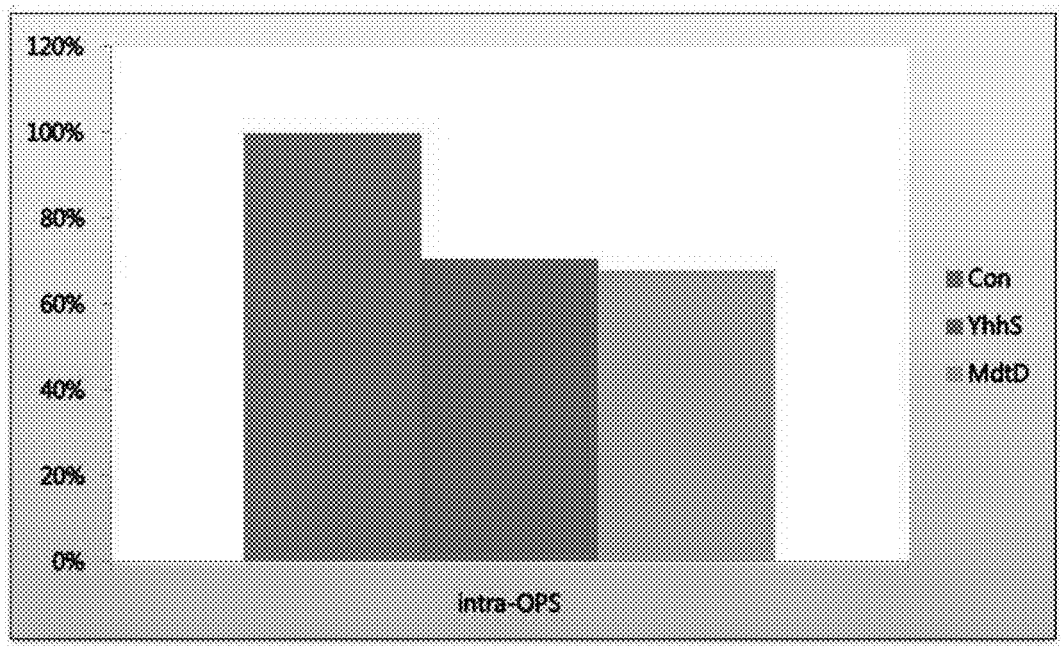

SEQUENCE LISTING

<160> NUMBER OF SEQ ID NOS: 34

<210> SEQ ID NO 1
<211> LENGTH: 405
<212> TYPE: PRT
<213> ORGANISM: Escherichia coli
<220> FEATURE:
<221> NAME/KEY: PEPTIDE
<222> LOCATION: (1)..(405)
<223> OTHER INFORMATION: YhhS MFS transporter, YhhS

<400> SEQUENCE: 1

```
Met Pro Glu Pro Val Ala Glu Pro Ala Leu Asn Gly Leu Arg Leu Asn
1               5                   10                  15

Leu Arg Ile Val Ser Ile Val Met Phe Asn Phe Ala Ser Tyr Leu Thr
            20                  25                  30

Ile Gly Leu Pro Leu Ala Val Leu Pro Gly Tyr Val His Asp Val Met
        35                  40                  45

Gly Phe Ser Ala Phe Trp Ala Gly Leu Val Ile Ser Leu Gln Tyr Phe
    50                  55                  60

Ala Thr Leu Leu Ser Arg Pro His Ala Gly Arg Tyr Ala Asp Ser Leu
65                  70                  75                  80

Gly Pro Lys Lys Ile Val Val Phe Gly Leu Cys Gly Cys Phe Leu Ser
                85                  90                  95

Gly Leu Gly Tyr Leu Thr Ala Gly Leu Thr Ala Ser Leu Pro Val Ile
            100                 105                 110

Ser Leu Leu Leu Leu Cys Leu Gly Arg Val Ile Leu Gly Ile Gly Gln
        115                 120                 125

Ser Phe Ala Gly Thr Gly Ser Thr Leu Trp Gly Val Gly Val Val Gly
    130                 135                 140

Ser Leu His Ile Gly Arg Val Ile Ser Trp Asn Gly Ile Val Thr Tyr
145                 150                 155                 160

Gly Ala Met Ala Met Gly Ala Pro Leu Gly Val Val Phe Tyr His Trp
                165                 170                 175

Gly Gly Leu Gln Ala Leu Ala Leu Ile Ile Met Gly Val Ala Leu Val
            180                 185                 190

Ala Ile Leu Leu Ala Ile Pro Arg Pro Thr Val Lys Ala Ser Lys Gly
        195                 200                 205

Lys Pro Leu Pro Phe Arg Ala Val Leu Gly Arg Val Trp Leu Tyr Gly
```

```
                210                 215                 220
Met Ala Leu Ala Leu Ala Ser Ala Gly Phe Gly Val Ile Ala Thr Phe
225                 230                 235                 240

Ile Thr Leu Phe Tyr Asp Ala Lys Gly Trp Asp Gly Ala Ala Phe Ala
                245                 250                 255

Leu Thr Leu Phe Ser Cys Ala Phe Val Gly Thr Arg Leu Leu Phe Pro
                260                 265                 270

Asn Gly Ile Asn Arg Ile Gly Gly Leu Asn Val Ala Met Ile Cys Phe
                275                 280                 285

Ser Val Glu Ile Ile Gly Leu Leu Val Gly Val Ala Thr Met Pro
                290                 295                 300

Trp Met Ala Lys Ile Gly Val Leu Leu Ala Gly Ala Gly Phe Ser Leu
305                 310                 315                 320

Val Phe Pro Ala Leu Gly Val Val Ala Val Lys Ala Val Pro Gln Gln
                325                 330                 335

Asn Gln Gly Ala Ala Leu Ala Thr Tyr Thr Val Phe Met Asp Leu Ser
                340                 345                 350

Leu Gly Val Thr Gly Pro Leu Ala Gly Leu Val Met Ser Trp Ala Gly
                355                 360                 365

Val Pro Val Ile Tyr Leu Ala Ala Gly Leu Val Ala Ile Ala Leu
                370                 375                 380

Leu Leu Thr Trp Arg Leu Lys Lys Arg Pro Pro Glu His Val Pro Glu
385                 390                 395                 400

Ala Ala Ser Ser Ser
                405

<210> SEQ ID NO 2
<211> LENGTH: 471
<212> TYPE: PRT
<213> ORGANISM: Escherichia coli
<220> FEATURE:
<221> NAME/KEY: PEPTIDE
<222> LOCATION: (1)..(471)
<223> OTHER INFORMATION: YegB MFS transporter, MdtD

<400> SEQUENCE: 2

Met Thr Asp Leu Pro Asp Ser Thr Arg Trp Gln Leu Trp Ile Val Ala
1               5                   10                  15

Phe Gly Phe Phe Met Gln Ser Leu Asp Thr Thr Ile Val Asn Thr Ala
                20                  25                  30

Leu Pro Ser Met Ala Gln Ser Leu Gly Glu Ser Pro Leu His Met His
                35                  40                  45

Met Val Ile Val Ser Tyr Val Leu Thr Val Ala Val Met Leu Pro Ala
    50                  55                  60

Ser Gly Trp Leu Ala Asp Lys Val Gly Val Arg Asn Ile Phe Phe Thr
65                  70                  75                  80

Ala Ile Val Leu Phe Thr Leu Gly Ser Leu Phe Cys Ala Leu Ser Gly
                85                  90                  95

Thr Leu Asn Glu Leu Leu Leu Ala Arg Ala Leu Gln Gly Val Gly Gly
                100                 105                 110

Ala Met Met Val Pro Val Gly Arg Leu Thr Val Met Lys Ile Val Pro
                115                 120                 125

Arg Glu Gln Tyr Met Ala Ala Met Thr Phe Val Thr Leu Pro Gly Gln
                130                 135                 140

Val Gly Pro Leu Leu Gly Pro Ala Leu Gly Gly Leu Leu Val Glu Tyr
145                 150                 155                 160
```

Ala Ser Trp His Trp Ile Phe Leu Ile Asn Ile Pro Val Gly Ile Ile
            165                 170                 175

Gly Ala Ile Ala Thr Leu Leu Leu Met Pro Asn Tyr Thr Met Gln Thr
        180                 185                 190

Arg Arg Phe Asp Leu Ser Gly Phe Leu Leu Ala Val Gly Met Ala
    195                 200                 205

Val Leu Thr Leu Ala Leu Asp Gly Ser Lys Gly Thr Gly Leu Ser Pro
210                 215                 220

Leu Thr Ile Ala Gly Leu Val Ala Val Gly Val Ala Leu Val Leu
225                 230                 235                 240

Tyr Leu Leu His Ala Arg Asn Asn Asn Arg Ala Leu Phe Ser Leu Lys
                245                 250                 255

Leu Phe Arg Thr Arg Thr Phe Ser Leu Gly Leu Ala Gly Ser Phe Ala
            260                 265                 270

Gly Arg Ile Gly Ser Gly Met Leu Pro Phe Met Thr Pro Val Phe Leu
        275                 280                 285

Gln Ile Gly Leu Gly Phe Ser Pro Phe His Ala Gly Leu Met Met Ile
    290                 295                 300

Pro Met Val Leu Gly Ser Met Gly Met Lys Arg Ile Val Gln Val
305                 310                 315                 320

Val Asn Arg Phe Gly Tyr Arg Arg Val Leu Val Ala Thr Thr Leu Gly
                325                 330                 335

Leu Ser Leu Val Thr Leu Leu Phe Met Thr Thr Ala Leu Leu Gly Trp
            340                 345                 350

Tyr Tyr Val Leu Pro Phe Val Leu Phe Leu Gln Gly Met Val Asn Ser
        355                 360                 365

Thr Arg Phe Ser Ser Met Asn Thr Leu Thr Leu Lys Asp Leu Pro Asp
    370                 375                 380

Asn Leu Ala Ser Ser Gly Asn Ser Leu Leu Ser Met Ile Met Gln Leu
385                 390                 395                 400

Ser Met Ser Ile Gly Val Thr Ile Ala Gly Leu Leu Leu Gly Leu Phe
                405                 410                 415

Gly Ser Gln His Val Ser Val Asp Ser Gly Thr Thr Thr Val Phe
            420                 425                 430

Met Tyr Thr Trp Leu Ser Met Ala Leu Ile Ile Ala Leu Pro Ala Phe
        435                 440                 445

Ile Phe Ala Arg Val Pro Asn Asp Thr His Gln Asn Val Ala Ile Ser
    450                 455                 460

Arg Arg Lys Arg Ser Ala Gln
465                 470

<210> SEQ ID NO 3
<211> LENGTH: 1218
<212> TYPE: DNA
<213> ORGANISM: Escherichia coli
<220> FEATURE:
<221> NAME/KEY: gene
<222> LOCATION: (1)..(1218)
<223> OTHER INFORMATION: yhhS

<400> SEQUENCE: 3
atgcccgaac ccgtagccga acccgcgcta aacggattgc gcctgaattt gcgcattgtc      60
tctatagtca tgtttaactt cgccagctac ctcaccatcg ggttgccgct cgctgtatta     120
ccgggctatg tccatgatgt gatgggcttt agcgccttct gggcaggatt ggttatcagc     180

| | |
|---|---|
| ctgcaatatt tcgccacctt gctgagccgc cctcatgccg acgttacgc cgattcgctg | 240 |
| ggacccaaaa agattgtcgt cttcggttta tgcggctgct ttttgagcgg tctggggtat | 300 |
| ctgacggcag gattaaccgc cagtctgcct gtcatcagcc tgttattact ttgcctgggg | 360 |
| cgcgtcatcc ttgggattgg gcaaagtttt gccggaacgg gatcgaccct atggggcgtt | 420 |
| ggcgtggttg gctcgctgca tatcgggcgg gtgatttcgt ggaacggcat tgtcacttac | 480 |
| ggggcgatgg cgatgggtgc gccgttaggc gtcgtgtttt atcactgggg cggcttgcag | 540 |
| gcgttagcgt taatcattat gggcgtggcg ctggtggcca ttttgttggc gatcccgcgt | 600 |
| ccgacggtaa aagccagtaa aggcaaaccg ctgccgtttc gcgcggtgct tgggcgcgtc | 660 |
| tggctgtacg gtatggcgct ggcactggct tccgccggat ttggcgtcat cgccacctttt | 720 |
| atcacgctgt tttatgacgc taaaggttgg gacggtgcgg cttcgcgct gacgctgttt | 780 |
| agctgtgcgt ttgtcggtac gcgtttgtta ttccctaacg gcattaaccg tatcggtggc | 840 |
| ttaaacgtag cgatgatttg ctttagcgtt gagataatcg gcctgctact ggttggcgtg | 900 |
| gcgactatgc cgtggatggc gaaaatcggc gtcttactgg cgggggccgg gttttcgctg | 960 |
| gtgttcccgg cattgggtgt agtggcggta aaagcggttc cgcagcaaaa tcaggggcg | 1020 |
| gcgctggcaa cttacaccgt atttatggat ttatcgcttg gcgtgactgg accactggct | 1080 |
| gggctggtga tgagctgggc gggcgtaccg gtgatttatc tggcggcggc gggactggtc | 1140 |
| gcaatcgcgt tattactgac gtggcgatta aaaaaacggc ctccggaaca cgtccctgag | 1200 |
| gccgcctcat catcttaa | 1218 |

<210> SEQ ID NO 4
<211> LENGTH: 1416
<212> TYPE: DNA
<213> ORGANISM: Escherichia coli
<220> FEATURE:
<221> NAME/KEY: gene
<222> LOCATION: (1)..(1416)
<223> OTHER INFORMATION: mdtD

<400> SEQUENCE: 4

| | |
|---|---|
| atgacagatc ttcccgacag cacccgttgg caattgtgga ttgtggcttt cggcttctttt | 60 |
| atgcagtcgc tggacaccac catcgtaaac accgcccttc cctcaatggc gcaaagcctc | 120 |
| ggggaaagtc cgttgcatat gcacatggtc attgtctctt atgtgctgac cgtggcggtg | 180 |
| atgctgcccg ccagcggctg gctggcggac aaagtcggcg tgcgcaatat tttctttacc | 240 |
| gccatcgtgc tgtttactct cggttcactg ttttgcgcgc tttccggcac gctgaacgaa | 300 |
| ctgttgctgg cacgcgcgtt acagggcgtt ggcgcgcga tgatggtgcc ggtcggcaga | 360 |
| ttgacggtga tgaaaatcgt accgcgcgag caatatatgg cggcgatgac ctttgtcacg | 420 |
| ttacccggtc aggtcggtcc gctgctcggt ccggcgctcg gcggtctgct ggtggagtac | 480 |
| gcatcgtggc actggatctt tttgatcaac attccggtgg ggattatcgg tgcgatcgcc | 540 |
| acattgctgt taatgccgaa ctacaccatg cagacgcggc gctttgatct ctccggatttt | 600 |
| ttattgctgg cggttggcat ggcggtatta accctggcgc tggacggcag taaaggtaca | 660 |
| ggtttatcgc cgctgacgat tgcaggcctg gtcgcagttg gcgtggtggc actggtgctt | 720 |
| tatctgctgc acgccagaaa taacaaccgt gccctgttca gtctgaaact gttccgtact | 780 |
| cgtacctttt cgctgggcct ggcggggagc tttgccggac gtattggcag tggcatgttg | 840 |
| cccctttatga caccggtttt cctgcaaatt ggcctcggtt tctcgccgtt tcatgccgga | 900 |
| ctgatgatga tcccgatggt gcttggcagc atgggaatga agcgaattgt ggtacaggtg | 960 |

```
gtgaatcgct ttggttatcg tcgggtactg gtagcgacca cgctgggtct gtcgctggtc    1020
accctgttgt ttatgactac cgccctgctg ggctggtact acgttttgcc gttcgtcctg    1080
tttttacaag ggatggtcaa ctcgacgcgt ttctcctcca tgaacaccct gacgctgaaa    1140
gatctcccgg acaatctggc gagcagcggc aacagcctgc tgtcgatgat tatgcaattg    1200
tcgatgagta tcggcgtcac tatcgccggg ctgttgctgg acttttttgg ttcacagcat    1260
gtcagcgtcg acagcggcac cacacaaacc gtctttatgt acacctggct tagcatggcg    1320
ttgatcatcg cccttccggc gttcatcttt gccagagtgc cgaacgatac gcatcaaaat    1380
gtagctattt cgcggcgaaa aaggagcgcg caatga                              1416
```

<210> SEQ ID NO 5
<211> LENGTH: 23
<212> TYPE: DNA
<213> ORGANISM: Artificial Sequence
<220> FEATURE:
<223> OTHER INFORMATION: primer for amplification of yhhS to construct
      pCL-PrhtB-yhhS

<400> SEQUENCE: 5

```
gatatcatgc ccgaacccgt agc                                              23
```

<210> SEQ ID NO 6
<211> LENGTH: 26
<212> TYPE: DNA
<213> ORGANISM: Artificial Sequence
<220> FEATURE:
<223> OTHER INFORMATION: primer for amplification of yhhS to construct
      pCL-PrhtB-yhhS

<400> SEQUENCE: 6

```
aagcttttaa gatgatgagg cggcct                                           26
```

<210> SEQ ID NO 7
<211> LENGTH: 27
<212> TYPE: DNA
<213> ORGANISM: Artificial Sequence
<220> FEATURE:
<223> OTHER INFORMATION: primer for amplification of mdtD to construct
      pCL-PrhtB-mdtD

<400> SEQUENCE: 7

```
gatatcatga cagatcttcc cgacagc                                          27
```

<210> SEQ ID NO 8
<211> LENGTH: 23
<212> TYPE: DNA
<213> ORGANISM: Artificial Sequence
<220> FEATURE:
<223> OTHER INFORMATION: primer for amplification of mdtD to construct
      pCL-PrhtB-mdtD

<400> SEQUENCE: 8

```
aagctttcat tgcgcgctcc ttt                                              23
```

<210> SEQ ID NO 9
<211> LENGTH: 24
<212> TYPE: DNA
<213> ORGANISM: Artificial Sequence
<220> FEATURE:
<223> OTHER INFORMATION: primer for amplification of rhtB to construct
      pCL-PrhtB-rhtB

<400> SEQUENCE: 9

```
gatatcatga ccttagaatg gtgg                                           24

<210> SEQ ID NO 10
<211> LENGTH: 24
<212> TYPE: DNA
<213> ORGANISM: Artificial Sequence
<220> FEATURE:
<223> OTHER INFORMATION: primer for amplification of rhtB to construct
      pCL-PrhtB-rhtB

<400> SEQUENCE: 10
aagctttcac gcatgcctcg ccga                                           24

<210> SEQ ID NO 11
<211> LENGTH: 29
<212> TYPE: DNA
<213> ORGANISM: Artificial Sequence
<220> FEATURE:
<223> OTHER INFORMATION: primer for amplification of emrD to construct
      pCL-PrhtB-emrD

<400> SEQUENCE: 11
gatatcatga aaaggcaaag aaacgtcaa                                      29

<210> SEQ ID NO 12
<211> LENGTH: 23
<212> TYPE: DNA
<213> ORGANISM: Artificial Sequence
<220> FEATURE:
<223> OTHER INFORMATION: primer for amplification of emrD to construct
      pCL-PrhtB-emrD

<400> SEQUENCE: 12
aagcttttaa acgggctgcc cct                                            23

<210> SEQ ID NO 13
<211> LENGTH: 28
<212> TYPE: DNA
<213> ORGANISM: Artificial Sequence
<220> FEATURE:
<223> OTHER INFORMATION: primer for amplification of ycaD to construct
      pCL-PrhtB-ycaD

<400> SEQUENCE: 13
gatatcatgt ccacgtatac ccagcctg                                       28

<210> SEQ ID NO 14
<211> LENGTH: 27
<212> TYPE: DNA
<213> ORGANISM: Artificial Sequence
<220> FEATURE:
<223> OTHER INFORMATION: primer for amplification of ycaD to construct
      pCL-PrhtB-ycaD

<400> SEQUENCE: 14
aagcttttac acgtgagcaa cgggttt                                        27

<210> SEQ ID NO 15
<211> LENGTH: 27
<212> TYPE: DNA
<213> ORGANISM: Artificial Sequence
<220> FEATURE:
<223> OTHER INFORMATION: primer for amplification of pCL-PrhtB-genes to
      constrct pCL-Prmf-serA(G336V)-serC_PrhtB-genes

<400> SEQUENCE: 15
```

```
aagcttcgggg cctcttcgct attacgc                                          27
```

<210> SEQ ID NO 16
<211> LENGTH: 27
<212> TYPE: DNA
<213> ORGANISM: Artificial Sequence
<220> FEATURE:
<223> OTHER INFORMATION: primer for amplification of pCL-PrhtB-genes to
      constrct pCL-Prmf-serA(G336V)-serC_PrhtB-genes

<400> SEQUENCE: 16

```
aagcttaggc ttacccgtct tactgtc                                           27
```

<210> SEQ ID NO 17
<211> LENGTH: 446
<212> TYPE: PRT
<213> ORGANISM: Corynebacterium glutamicum
<220> FEATURE:
<221> NAME/KEY: PEPTIDE
<222> LOCATION: (1)..(446)
<223> OTHER INFORMATION: phosphoserine phosphatase, SerB

<400> SEQUENCE: 17

```
Met Ser Cys Ser Ala Leu Arg His Glu Thr Ile Val Ala Val Thr Glu
1               5                   10                  15

Leu Ile Gln Asn Glu Ser Gln Glu Ile Ala Glu Leu Glu Ala Gly Gln
            20                  25                  30

Gln Val Ala Leu Arg Glu Gly Tyr Leu Pro Ala Val Ile Thr Val Ser
        35                  40                  45

Gly Lys Asp Arg Pro Gly Val Thr Ala Ala Phe Phe Arg Val Leu Ser
    50                  55                  60

Ala Asn Gln Val Gln Val Leu Asp Val Glu Gln Ser Met Phe Arg Gly
65                  70                  75                  80

Phe Leu Asn Leu Ala Ala Phe Val Gly Ile Ala Pro Glu Arg Val Glu
                85                  90                  95

Thr Val Thr Thr Gly Leu Thr Asp Thr Leu Lys Val His Gly Gln Ser
            100                 105                 110

Val Val Val Glu Leu Gln Glu Thr Val Gln Ser Ser Arg Pro Arg Ser
        115                 120                 125

Ser His Val Val Val Leu Gly Asp Pro Val Asp Ala Leu Asp Ile
    130                 135                 140

Ser Arg Ile Gly Gln Thr Leu Ala Asp Tyr Asp Ala Asn Ile Asp Thr
145                 150                 155                 160

Ile Arg Gly Ile Ser Asp Tyr Pro Val Thr Gly Leu Glu Leu Lys Val
                165                 170                 175

Thr Val Pro Asp Val Ser Pro Gly Gly Gly Glu Ala Met Arg Lys Ala
            180                 185                 190

Leu Ala Ala Leu Thr Ser Glu Leu Asn Val Asp Ile Ala Ile Glu Arg
        195                 200                 205

Ser Gly Leu Leu Arg Arg Ser Lys Arg Leu Val Cys Phe Asp Cys Asp
    210                 215                 220

Ser Thr Leu Ile Thr Gly Glu Val Ile Glu Met Leu Ala Ala His Ala
225                 230                 235                 240

Gly Lys Glu Ala Glu Val Ala Val Thr Glu Arg Ala Met Arg Gly
                245                 250                 255

Glu Leu Asp Phe Glu Glu Ser Leu Arg Glu Arg Val Lys Ala Leu Ala
            260                 265                 270

Gly Leu Asp Ala Ser Val Ile Asp Glu Val Ala Ala Ala Ile Glu Leu
```

```
                     275                 280                 285
Thr Pro Gly Ala Arg Thr Thr Ile Arg Thr Leu Asn Arg Met Gly Tyr
    290                 295                 300
Gln Thr Ala Val Val Ser Gly Gly Phe Ile Gln Val Leu Glu Gly Leu
305                 310                 315                 320
Ala Glu Glu Leu Glu Leu Asp Tyr Val Arg Ala Asn Thr Leu Glu Ile
                325                 330                 335
Val Asp Gly Lys Leu Thr Gly Asn Val Thr Gly Lys Ile Val Asp Arg
            340                 345                 350
Ala Ala Lys Ala Glu Phe Leu Arg Glu Phe Ala Asp Ser Gly Leu
        355                 360                 365
Lys Met Tyr Gln Thr Val Ala Val Gly Asp Gly Ala Asn Asp Ile Asp
    370                 375                 380
Met Leu Ser Ala Ala Gly Leu Gly Val Ala Phe Asn Ala Lys Pro Ala
385                 390                 395                 400
Leu Lys Glu Ile Ala Asp Thr Ser Val Asn His Pro Phe Leu Asp Glu
                405                 410                 415
Val Leu His Ile Met Gly Ile Ser Arg Asp Glu Ile Asp Leu Ala Asp
            420                 425                 430
Gln Glu Asp Gly Thr Phe His Arg Val Pro Leu Thr Asn Ala
        435                 440                 445

<210> SEQ ID NO 18
<211> LENGTH: 322
<212> TYPE: PRT
<213> ORGANISM: Escherichia coli
<220> FEATURE:
<221> NAME/KEY: PEPTIDE
<222> LOCATION: (1)..(322)
<223> OTHER INFORMATION: phosphoserine phosphatase, SerB

<400> SEQUENCE: 18

Met Pro Asn Ile Thr Trp Cys Asp Leu Pro Glu Asp Val Ser Leu Trp
1               5                   10                  15
Pro Gly Leu Pro Leu Ser Leu Ser Gly Asp Glu Val Met Pro Leu Asp
                20                  25                  30
Tyr His Ala Gly Arg Ser Gly Trp Leu Leu Tyr Gly Arg Gly Leu Asp
            35                  40                  45
Lys Gln Arg Leu Thr Gln Tyr Gln Ser Lys Leu Gly Ala Ala Met Val
        50                  55                  60
Ile Val Ala Ala Trp Cys Val Glu Asp Tyr Gln Val Ile Arg Leu Ala
65                  70                  75                  80
Gly Ser Leu Thr Ala Arg Ala Thr Arg Leu Ala His Glu Ala Gln Leu
                85                  90                  95
Asp Val Ala Pro Leu Gly Lys Ile Pro His Leu Arg Thr Pro Gly Leu
            100                 105                 110
Leu Val Met Asp Met Asp Ser Thr Ala Ile Gln Ile Glu Cys Ile Asp
        115                 120                 125
Glu Ile Ala Lys Leu Ala Gly Thr Gly Glu Met Val Ala Glu Val Thr
    130                 135                 140
Glu Arg Ala Met Arg Gly Glu Leu Asp Phe Thr Ala Ser Leu Arg Ser
145                 150                 155                 160
Arg Val Ala Thr Leu Lys Gly Ala Asp Ala Asn Ile Leu Gln Gln Val
                165                 170                 175
Arg Glu Asn Leu Pro Leu Met Pro Gly Leu Thr Gln Leu Val Leu Lys
            180                 185                 190
```

```
Leu Glu Thr Leu Gly Trp Lys Val Ala Ile Ala Ser Gly Gly Phe Thr
            195                 200                 205

Phe Phe Ala Glu Tyr Leu Arg Asp Lys Leu Arg Leu Thr Ala Val Val
    210                 215                 220

Ala Asn Glu Leu Glu Ile Met Asp Gly Lys Phe Thr Gly Asn Val Ile
225                 230                 235                 240

Gly Asp Ile Val Asp Ala Gln Tyr Lys Ala Lys Thr Leu Thr Arg Leu
                245                 250                 255

Ala Gln Glu Tyr Glu Ile Pro Leu Ala Gln Thr Val Ala Ile Gly Asp
            260                 265                 270

Gly Ala Asn Asp Leu Pro Met Ile Lys Ala Ala Gly Leu Gly Ile Ala
            275                 280                 285

Tyr His Ala Lys Pro Lys Val Asn Glu Lys Ala Glu Val Thr Ile Arg
            290                 295                 300

His Ala Asp Leu Met Gly Val Phe Cys Ile Leu Ser Gly Ser Leu Asn
305                 310                 315                 320

Gln Lys
```

<210> SEQ ID NO 19
<211> LENGTH: 1341
<212> TYPE: DNA
<213> ORGANISM: Corynebacterium glutamicum
<220> FEATURE:
<221> NAME/KEY: gene
<222> LOCATION: (1)..(1341)
<223> OTHER INFORMATION: phosphoserine phosphatase, SerB

<400> SEQUENCE: 19

```
atgtcgtgtt ccgcgctcag acatgagaca attgttgccg tgactgaact catccagaat      60
gaatcccaag aaatcgctga gctggaagcc ggccagcagg ttgcattgcg tgaaggttat     120
cttcctgcgg tgatcacagt gagcggtaaa gaccgcccag gtgtgactgc cgcgttcttt     180
agggtcttgt ccgctaatca ggttcaggtc ttggacgttg agcagtcaat gttccgtggc     240
tttttgaact tggcggcgtt tgtgggtatc gcacctgagc gtgtcgagac cgtcaccaca     300
ggcctgactg acaccctcaa ggtgcatgga cagtccgtgg tggtggagct gcaggaaact     360
gtgcagtcgt cccgtcctcg ttcttcccat gttgttgtgg tgttgggtga tccggttgat     420
gcgttggata tttcccgcat tggtcagacc ctggcggatt acgatgccaa cattgacacc     480
attcgtggta tttcggatta ccctgtgacc ggcctggagc tgaaggtgac tgtgccggat     540
gtcagccctg gtggtggtga agcgatgcgt aaggcgcttg ctgctcttac ctctgagctg     600
aatgtggata ttgcgattga gcgttctggt ttgctgcgtc gttctaagcg tctggtgtgc     660
ttcgattgtg attccacgtt gatcactggt gaggtcattg agatgctggc ggctcacgcg     720
ggcaaggaag ctgaagttgc ggcagttact gagcgtgcga tgcgcggtga gctcgatttc     780
gaggagtctc tgcgtgagcg tgtgaaggcg ttggctggtt tggatgcgtc ggtgatcgat     840
gaggtcgctg ccgctattga gctgaccect ggtgcgcgca ccacgatccg tacgctgaac     900
cgcatgggtt accagaccgc tgttgtttcc ggtggtttca tccaggtgtt ggaaggtttg     960
gctgaggagt tggagttgga ttatgtccgc gccaacactt tggaaatcgt tgatggcaag    1020
ctgaccggca acgtcaccgg aaagatcgtt gaccgcgctg cgaaggctga gttcctccgt    1080
gagttcgctg cggattctgg cctgaagatg taccagactg tcgctgtcgg tgatggcgct    1140
aatgacatcg atatgctctc cgctgcgggt ctgggtgttg ctttcaacgc gaagcctgcg    1200
```

```
ctgaaggaga ttgcggatac ttccgtgaac cacccattcc tcgacgaggt tttgcacatc    1260
atgggcattt cccgcgacga gatcgatctg gcggatcagg aagacggcac tttccaccgc    1320
gttccattga ccaatgccta a                                              1341
```

<210> SEQ ID NO 20
<211> LENGTH: 969
<212> TYPE: DNA
<213> ORGANISM: Escherichia coli
<220> FEATURE:
<221> NAME/KEY: gene
<222> LOCATION: (1)..(969)
<223> OTHER INFORMATION: phosphoserine phosphatase, SerB

<400> SEQUENCE: 20

```
atgcctaaca ttacctggtg cgacctgcct gaagatgtct ctttatggcc gggtctgcct     60
ctttcattaa gtggtgatga agtgatgcca ctggattacc acgcaggtcg tagcggctgg    120
ctgctgtatg gtcgtgggct ggataaacaa cgtctgaccc aataccagag caaactgggt    180
gcggcgatgg tgattgttgc cgcctggtgc gtggaagatt atcaggtgat tcgtctggca    240
ggttcactca ccgcacgggc tacacgcctg gcccacgaag cgcagctgga tgtcgccccg    300
ctggggaaaa tcccgcacct gcgcacgccg ggtttgctgg tgatggatat ggactccacc    360
gccatccaga ttgaatgtat tgatgaaatt gccaaactgg ccggaacggg cgagatggtg    420
gcggaagtaa ccgaacgggc gatgcgcggc gaactcgatt ttaccgccag cctgcgcagc    480
cgtgtggcga cgctgaaagg cgctgacgcc aatattctgc aacaggtgcg tgaaaatctg    540
ccgctgatgc caggcttaac gcaactggtg ctcaagctgg aaacgctggg ctggaaagtg    600
gcgattgcct ccggcggctt tacttctttt gctgaatacc tgcgcgacaa gctgcgcctg    660
accgccgtgg tagccaatga actggagatc atggacggta aatttaccgg caatgtgatc    720
ggcgacatcg tagacgcgca gtacaaagcg aaaactctga ctcgcctcgc gcaggagtat    780
gaaatcccgc tggcgcagac cgtggcgatt ggcgatggag ccaatgacct gccgatgatc    840
aaagcggcag ggctggggat tgcctaccat gccaagccaa agtgaatga aaaggcggaa    900 gtcaccatcc gtcacgctga cctgatgggg gtattctgca tcctctcagg cagcctgaat    960
cagaagtaa                                                            969
```

<210> SEQ ID NO 21
<211> LENGTH: 410
<212> TYPE: PRT
<213> ORGANISM: Escherichia coli
<220> FEATURE:
<221> NAME/KEY: PEPTIDE
<222> LOCATION: (1)..(410)
<223> OTHER INFORMATION: SerA

<400> SEQUENCE: 21

```
Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
65                  70                  75                  80
```

```
Cys Phe Cys Ile Gly Thr Asn Gln Val Asp Leu Asp Ala Ala Ala Lys
                85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Arg Gly Val Pro
        115                 120                 125

Glu Ala Asn Ala Lys Ala His Arg Gly Val Trp Asn Lys Leu Ala Ala
    130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
            180                 185                 190

Gln Val Gln His Leu Ser Asp Leu Leu Asn Met Ser Asp Val Val Ser
        195                 200                 205

Leu His Val Pro Glu Asn Pro Ser Thr Lys Asn Met Met Gly Ala Lys
    210                 215                 220

Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
                245                 250                 255

His Leu Ala Gly Ala Ala Ile Asp Val Phe Pro Thr Glu Pro Ala Thr
            260                 265                 270

Asn Ser Asp Pro Phe Thr Ser Pro Leu Cys Glu Phe Asp Asn Val Leu
        275                 280                 285

Leu Thr Pro His Ile Gly Gly Ser Thr Gln Glu Ala Gln Glu Asn Ile
    290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Gly
                325                 330                 335

Gly Arg Arg Leu Met His Ile His Glu Asn Arg Pro Gly Val Leu Thr
            340                 345                 350

Ala Leu Asn Lys Ile Phe Ala Glu Gln Gly Val Asn Ile Ala Ala Gln
        355                 360                 365

Tyr Leu Gln Thr Ser Ala Gln Met Gly Tyr Val Val Ile Asp Ile Glu
    370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
                405                 410

<210> SEQ ID NO 22
<211> LENGTH: 530
<212> TYPE: PRT
<213> ORGANISM: Artificial Sequence
<220> FEATURE:
<223> OTHER INFORMATION: Modified D-3-phosphoglycerate
      dehydrogenase(E235K), SerA(E235K)

<400> SEQUENCE: 22

Met Ser Gln Asn Gly Arg Pro Val Val Leu Ile Ala Asp Lys Leu Ala
1               5                   10                  15

Gln Ser Thr Val Asp Ala Leu Gly Asp Ala Val Glu Val Arg Trp Val
            20                  25                  30
```

```
Asp Gly Pro Asn Arg Pro Glu Leu Leu Asp Ala Val Lys Glu Ala Asp
        35                  40                  45

Ala Leu Leu Val Arg Ser Ala Thr Thr Val Asp Ala Glu Val Ile Ala
 50                  55                  60

Ala Ala Pro Asn Leu Lys Ile Val Gly Arg Ala Gly Val Gly Leu Asp
 65                  70                  75                  80

Asn Val Asp Ile Pro Ala Ala Thr Glu Ala Gly Val Met Val Ala Asn
                 85                  90                  95

Ala Pro Thr Ser Asn Ile His Ser Ala Cys Glu His Ala Ile Ser Leu
             100                 105                 110

Leu Leu Ser Thr Ala Arg Gln Ile Pro Ala Ala Asp Ala Thr Leu Arg
             115                 120                 125

Glu Gly Glu Trp Lys Arg Ser Ser Phe Asn Gly Val Glu Ile Phe Gly
         130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
                 165                 170                 175

Ala Asn Pro Ala Arg Ala Ala Gln Leu Asn Val Glu Leu Val Glu Leu
             180                 185                 190

Asp Glu Leu Met Ser Arg Ser Asp Phe Val Thr Ile His Leu Pro Lys
         195                 200                 205

Thr Lys Glu Thr Ala Gly Met Phe Asp Ala Gln Leu Leu Ala Lys Ser
210                 215                 220

Lys Lys Gly Gln Ile Ile Ile Asn Ala Ala Arg Gly Gly Leu Val Asp
225                 230                 235                 240

Glu Gln Ala Leu Ala Asp Ala Ile Glu Ser Gly His Ile Arg Gly Ala
                 245                 250                 255

Gly Phe Asp Val Tyr Ser Thr Glu Pro Cys Thr Asp Ser Pro Leu Phe
             260                 265                 270

Lys Leu Pro Gln Val Val Thr Pro His Leu Gly Ala Ser Thr Glu
         275                 280                 285

Glu Ala Gln Asp Arg Ala Gly Thr Asp Val Ala Asp Ser Val Leu Lys
290                 295                 300

Ala Leu Ala Gly Glu Phe Val Ala Asp Ala Val Asn Val Ser Gly Gly
305                 310                 315                 320

Arg Val Gly Glu Lys Val Ala Val Trp Met Asp Leu Ala Arg Lys Leu
                 325                 330                 335

Gly Leu Leu Ala Gly Lys Leu Val Asp Ala Ala Pro Val Ser Ile Glu
             340                 345                 350

Val Glu Ala Arg Gly Glu Leu Ser Ser Glu Gln Val Asp Ala Leu Gly
         355                 360                 365

Leu Ser Ala Val Arg Gly Leu Phe Ser Gly Ile Ile Glu Glu Ser Val
370                 375                 380

Thr Phe Val Asn Ala Pro Arg Ile Ala Glu Glu Arg Gly Leu Asp Ile
385                 390                 395                 400

Ser Val Lys Thr Asn Ser Glu Ser Val Thr His Arg Ser Val Leu Gln
                 405                 410                 415

Val Lys Val Ile Thr Gly Ser Gly Ala Ser Ala Thr Val Val Gly Ala
             420                 425                 430

Leu Thr Gly Leu Glu Arg Val Glu Lys Ile Thr Arg Ile Asn Gly Arg
         435                 440                 445
```

```
Gly Leu Asp Leu Arg Ala Glu Gly Leu Asn Leu Phe Leu Gln Tyr Thr
    450                 455                 460

Asp Ala Pro Gly Ala Leu Gly Thr Val Gly Thr Lys Leu Gly Ala Ala
465                 470                 475                 480

Gly Ile Asn Ile Glu Ala Ala Ala Leu Thr Gln Ala Glu Lys Gly Asp
                485                 490                 495

Gly Ala Val Leu Ile Leu Arg Val Glu Ser Ala Val Ser Glu Glu Leu
            500                 505                 510

Glu Ala Glu Ile Asn Ala Glu Leu Gly Ala Thr Ser Phe Gln Val Asp
        515                 520                 525

Leu Asp
    530
```

<210> SEQ ID NO 23
<211> LENGTH: 333
<212> TYPE: PRT
<213> ORGANISM: Artificial Sequence
<220> FEATURE:
<223> OTHER INFORMATION: Modified D-3-phosphoglycerate
      dehydrogenase(197 delta), SerA(197 delta)

<400> SEQUENCE: 23

```
Met Ser Gln Asn Gly Arg Pro Val Val Leu Ile Ala Asp Lys Leu Ala
1               5                   10                  15

Gln Ser Thr Val Asp Ala Leu Gly Asp Ala Val Glu Val Arg Trp Val
            20                  25                  30

Asp Gly Pro Asn Arg Pro Glu Leu Leu Asp Ala Val Lys Glu Ala Asp
        35                  40                  45

Ala Leu Leu Val Arg Ser Ala Thr Thr Val Asp Ala Glu Val Ile Ala
    50                  55                  60

Ala Ala Pro Asn Leu Lys Ile Val Gly Arg Ala Gly Val Gly Leu Asp
65                  70                  75                  80

Asn Val Asp Ile Pro Ala Ala Thr Glu Ala Gly Val Met Val Ala Asn
                85                  90                  95

Ala Pro Thr Ser Asn Ile His Ser Ala Cys Glu His Ala Ile Ser Leu
            100                 105                 110

Leu Leu Ser Thr Ala Arg Gln Ile Pro Ala Ala Asp Ala Thr Leu Arg
        115                 120                 125

Glu Gly Glu Trp Lys Arg Ser Ser Phe Asn Gly Val Glu Ile Phe Gly
    130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
                165                 170                 175

Ala Asn Pro Ala Arg Ala Ala Gln Leu Asn Val Glu Leu Val Glu Leu
            180                 185                 190

Asp Glu Leu Met Ser Arg Ser Asp Phe Val Thr Ile His Leu Pro Lys
        195                 200                 205

Thr Lys Glu Thr Ala Gly Met Phe Asp Ala Gln Leu Leu Ala Lys Ser
    210                 215                 220

Lys Lys Gly Gln Ile Ile Ile Asn Ala Ala Arg Gly Gly Leu Val Asp
225                 230                 235                 240

Glu Gln Ala Leu Ala Asp Ala Ile Glu Ser Gly His Ile Arg Gly Ala
                245                 250                 255

Gly Phe Asp Val Tyr Ser Thr Glu Pro Cys Thr Asp Ser Pro Leu Phe
            260                 265                 270
```

Lys Leu Pro Gln Val Val Thr Pro His Leu Gly Ala Ser Thr Glu
        275                 280                 285

Glu Ala Gln Asp Arg Ala Gly Thr Asp Val Ala Asp Ser Val Leu Lys
290                 295                 300

Ala Leu Ala Gly Glu Phe Val Ala Asp Ala Val Asn Val Ser Gly Gly
305                 310                 315                 320

Arg Val Gly Glu Glu Val Ala Val Trp Met Asp Leu Ala
                325                 330

<210> SEQ ID NO 24
<211> LENGTH: 410
<212> TYPE: PRT
<213> ORGANISM: Artificial Sequence
<220> FEATURE:
<223> OTHER INFORMATION: Modified D-3-phosphoglycerate
      dehydrogenase(G336V), SerA(G336V)

<400> SEQUENCE: 24

Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Ala Lys
                85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Leu Arg Gly Val Pro
        115                 120                 125

Glu Ala Asn Ala Lys Ala His Arg Gly Val Trp Asn Lys Leu Ala Ala
130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
            180                 185                 190

Gln Val Gln His Leu Ser Asp Leu Leu Asn Met Ser Asp Val Val Ser
        195                 200                 205

Leu His Val Pro Glu Asn Pro Ser Thr Lys Asn Met Met Gly Ala Lys
210                 215                 220

Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
                245                 250                 255

His Leu Ala Gly Ala Ala Ile Asp Val Phe Pro Thr Glu Pro Ala Thr
            260                 265                 270

Asn Ser Asp Pro Phe Thr Ser Pro Leu Cys Glu Phe Asp Asn Val Leu
        275                 280                 285

Leu Thr Pro His Ile Gly Gly Ser Thr Gln Glu Ala Gln Glu Asn Ile

```
                290                 295                 300
Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Val
                325                 330                 335

Gly Arg Arg Leu Met His Ile His Glu Asn Arg Pro Gly Val Leu Thr
            340                 345                 350

Ala Leu Asn Lys Ile Phe Ala Glu Gln Gly Val Asn Ile Ala Ala Gln
        355                 360                 365

Tyr Leu Gln Thr Ser Ala Gln Met Gly Tyr Val Val Ile Asp Ile Glu
370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
                405                 410

<210> SEQ ID NO 25
<211> LENGTH: 410
<212> TYPE: PRT
<213> ORGANISM: Artificial Sequence
<220> FEATURE:
<223> OTHER INFORMATION: Modified D-3-phosphoglycerate
      dehydrogenase(G336V, G337V), SerA(G336V, G337V)

<400> SEQUENCE: 25

Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Ala Lys
                85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Leu Arg Gly Val Pro
        115                 120                 125

Glu Ala Asn Ala Lys Ala His Arg Gly Val Trp Asn Lys Leu Ala Ala
    130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
            180                 185                 190

Gln Val Gln His Leu Ser Asp Leu Leu Asn Met Ser Asp Val Val Ser
        195                 200                 205

Leu His Val Pro Glu Asn Pro Ser Thr Lys Asn Met Met Gly Ala Lys
    210                 215                 220

Glu Ile Ser Leu Met Lys Pro Gly Ser Leu Leu Ile Asn Ala Ser Arg
225                 230                 235                 240
```

```
Gly Thr Val Val Asp Ile Pro Ala Leu Cys Asp Ala Leu Ala Ser Lys
            245                 250                 255

His Leu Ala Gly Ala Ala Ile Asp Val Phe Pro Thr Glu Pro Ala Thr
        260                 265                 270

Asn Ser Asp Pro Phe Thr Ser Pro Leu Cys Glu Phe Asp Asn Val Leu
    275                 280                 285

Leu Thr Pro His Ile Gly Gly Ser Thr Gln Glu Ala Gln Glu Asn Ile
290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Val
            325                 330                 335

Val Arg Arg Leu Met His Ile His Glu Asn Arg Pro Gly Val Leu Thr
        340                 345                 350

Ala Leu Asn Lys Ile Phe Ala Glu Gln Gly Val Asn Ile Ala Ala Gln
    355                 360                 365

Tyr Leu Gln Thr Ser Ala Gln Met Gly Tyr Val Val Ile Asp Ile Glu
370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
            405                 410

<210> SEQ ID NO 26
<211> LENGTH: 410
<212> TYPE: PRT
<213> ORGANISM: Artificial Sequence
<220> FEATURE:
<223> OTHER INFORMATION: Modified D-3-phosphoglycerate
      dehydrogenase(G336V, R338G), SerA(G336V, R338G)

<400> SEQUENCE: 26

Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Ala Lys
                85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Leu Arg Gly Val Pro
        115                 120                 125

Glu Ala Asn Ala Lys Ala His Arg Gly Val Trp Asn Lys Leu Ala Ala
    130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
            180                 185                 190
```

```
Gln Val Gln His Leu Ser Asp Leu Leu Asn Met Ser Asp Val Val Ser
            195                 200                 205

Leu His Val Pro Glu Asn Pro Ser Thr Lys Asn Met Met Gly Ala Lys
    210                 215                 220

Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
                245                 250                 255

His Leu Ala Gly Ala Ala Ile Asp Val Phe Pro Thr Glu Pro Ala Thr
            260                 265                 270

Asn Ser Asp Pro Phe Thr Ser Pro Leu Cys Glu Phe Asp Asn Val Leu
        275                 280                 285

Leu Thr Pro His Ile Gly Gly Ser Thr Gln Glu Ala Gln Glu Asn Ile
    290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Val
                325                 330                 335

Gly Gly Arg Leu Met His Ile His Glu Asn Arg Pro Gly Val Leu Thr
            340                 345                 350

Ala Leu Asn Lys Ile Phe Ala Glu Gln Gly Val Asn Ile Ala Ala Gln
        355                 360                 365

Tyr Leu Gln Thr Ser Ala Gln Met Gly Tyr Val Val Ile Asp Ile Glu
    370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
                405                 410

<210> SEQ ID NO 27
<211> LENGTH: 1233
<212> TYPE: DNA
<213> ORGANISM: Escherichia coli
<220> FEATURE:
<221> NAME/KEY: gene
<222> LOCATION: (1)..(1233)
<223> OTHER INFORMATION: SerA

<400> SEQUENCE: 27
atggcaaagg tatcgctgga aaagacaag  attaagtttc tgctggtaga aggcgtgcac      60
caaaaggcgc tggaaagcct tcgtgcagct ggttacacca acatcgaatt tcacaaaggc     120
gcgctggatg atgaacaatt aaaagaatcc atccgcgatg cccacttcat cggcctgcga     180
tcccgtaccc atctgactga agacgtgatc aacgccgcag aaaaactggt cgctattggc     240
tgtttctgta tcggaacaaa ccaggttgat ctggatgcgg cggcaaagcg cgggatcccg     300
gtatttaacg caccgttctc aaatacgcgc tctgttgcgg agctggtgat ggcgaactg      360 ctgctgctat gcgcggcgt gccggaagcc aatgctaaag cgcaccgtgg cgtgtggaac     420
aaactggcgg cgggttcttt tgaagcgcgc ggcaaaaagc tgggtatcat cggctacgtt     480
catattggta cgcaattggg cattctggct gaatcgctgg aatgtatgt ttactttttat    540 gatattgaaa ataaactgcc gctgggcaac gccactcagg tacagcatct ttctgacctg     600
ctgaatatga gcgatgtggt gagtctgcat gtaccagaga atccgtccac caaaaatatg     660
atgggcgcga agaaatttc actaatgaag cccggctcgc tgctgattaa tgcttcgcgc     720
```

```
ggtactgtgg tggatattcc ggcgctgtgt gatgcgctgg cgagcaaaca tctggcgggg      780
gcggcaatcg acgtattccc gacggaaccg gcgaccaata gcgatccatt tacctctccg      840
ctgtgtgaat tcgacaacgt ccttctgacg ccacacattg gcggttcgac tcaggaagcg      900
caggagaata tcggcctgga agttgcgggt aaattgatca agtattctga caatggctca      960
acgctctctg cggtgaactt cccggaagtc tcgctgccac tgcacggtgg cgtcgtctg     1020 atgcacatcc acgaaaaccg tccgggcgtg ctaactgcgc tgaacaaaat cttcgccgag     1080
cagggcgtca acatcgccgc gcaatatctg caaacttccg cccagatggg ttatgtggtt     1140
attgatattg aagccgacga agacgttgcc gaaaaagcgc tgcaggcaat gaaagctatt     1200
ccgggtacca ttcgcgcccg tctgctgtac taa                                   1233
```

<210> SEQ ID NO 28
<211> LENGTH: 1593
<212> TYPE: DNA
<213> ORGANISM: Artificial Sequence
<220> FEATURE:
<223> OTHER INFORMATION: Modified D-3-phosphoglycerate
      dehydrogenase(E235K), SerA(E235K)

<400> SEQUENCE: 28

```
atgagccaga atggccgtcc ggtagtcctc atcgccgata agcttgcgca gtccactgtt       60
gacgcgcttg gagatgcagt agaagtccgt tgggttgacg gacctaaccg cccagaactg      120
cttgatgcag ttaaggaagc ggacgcactg ctcgtgcgtt ctgctaccac tgtcgatgct      180
gaagtcatcg ccgctgcccc taacttgaag atcgtcggtc gtgccggcgt gggcttggac      240
aacgttgaca tccctgctgc cactgaagct ggcgtcatgg ttgctaacgc accgacctct      300
aatattcact ccgcttgtga gcacgcaatt tctttgctgc tgtctactgc tcgccagatc      360
cctgctgctg atgcgacgct gcgtgagggc gagtggaagc ggtcttcttt caacggtgtg      420
gaaattttcg gaaaaactgt cggtatcgtc ggttttggcc acattggtca gttgtttgct      480
cagcgtcttg ctgcgtttga gaccaccatt gttgcttacg atccttacgc taaccctgct      540
cgtgcggctc agctgaacgt tgagttggtt gagttggatg agctgatgag ccgttctgac      600
tttgtcacca ttcaccttcc taagaccaag gaaactgctg catgtttga tgcgcagctc      660 cttgctaagt ccaagaaggg ccagatcatc atcaacgctg ctcgtggtgg ccttgttgat      720
gagcaggctt ggctgatgc gattgagtcc ggtcacattc gtggcgctgg tttcgatgtg      780
tactccaccg agccttgcac tgattctcct ttgttcaagt gcctcaggt tgttgtgact       840 cctcacttgg gtgcttctac tgaagaggct caggatcgtg cgggtactga cgttgctgat      900
tctgtgctca aggcgctggc tggcgagttc gtggcggatg ctgtgaacgt ttccggtggt      960
cgcgtgggcg aaaaggttgc tgtgtggatg gatctggctc gcaagcttgg tcttcttgct     1020
ggcaagcttg tcgacgccgc cccagtctcc attgaggttg aggctcgagg cgagctttct     1080
tccgagcagg tcgatgcact tggttttgtcc gctgttcgtg gtttgttctc cggaattatc     1140
gaagagtccg ttactttcgt caacgctcct cgcattgctg aagagcgtgg cctggacatc     1200
tccgtgaaga ccaactctga gtctgttact caccgttccg tcctgcaggt caaggtcatt     1260
actggcagcg gcgcgagcgc aactgttgtt ggtgccctga ctggtcttga gcgcgttgag     1320
aagatcaccc gcatcaatgg ccgtggcctg gatctgcgcg cagagggtct gaacctcttc     1380
ctgcagtaca ctgacgctcc tggtgcactg gtaccgttg gtaccaagct gggtgctgct     1440
ggcatcaaca tcgaggctgc tgcgttgact caggctgaga agggtgacgg cgctgtcctg     1500
```

```
atcctgcgtg ttgagtccgc tgtctctgaa gagctggaag ctgaaatcaa cgctgagttg    1560
ggtgctactt ccttccaggt tgatcttgac taa                                 1593

<210> SEQ ID NO 29
<211> LENGTH: 1002
<212> TYPE: DNA
<213> ORGANISM: Artificial Sequence
<220> FEATURE:
<223> OTHER INFORMATION: Modified D-3-phosphoglycerate
      dehydrogenase(197 delta), SerA(197 delta)

<400> SEQUENCE: 29
atgagccaga atggccgtcc ggtagtcctc atcgccgata agcttgcgca gtccactgtt     60
gacgcgcttg agatgcagt agaagtccgt tgggttgacg acctaaccg cccagaactg      120 cttgatgcag ttaaggaagc ggacgcactg ctcgtgcgtt ctgctaccac tgtcgatgct   180
gaagtcatcg ccgctgcccc taacttgaag atcgtcggtc gtgccggcgt gggcttggac   240
aacgttgaca tccctgctgc cactgaagct ggcgtcatgg ttgctaacgc accgacctct   300
aatattcact ccgcttgtga gcacgcaatt tctttgctgc tgtctactgc tcgccagatc   360
cctgctgctg atgcgacgct gcgtgagggc gagtggaagc ggtcttcttt caacggtgtg   420
gaaattttcg gaaaaactgt cggtatcgtc ggttttggcc acattggtca gttgtttgct   480
cagcgtcttg ctgcgtttga gaccaccatt gttgcttacg atcctacgc taaccctgct   540 cgtgcggctc agctgaacgt tgagttggtt gagttggatg agctgatgag ccgttctgac   600
tttgtcacca ttcaccttcc taagaccaag gaaactgctg gcatgtttga tgcgcagctc   660
cttgctaagt ccaagaaggg ccagatcatc atcaacgctg ctcgtggtgg ccttgttgat   720
gagcaggctt ggctgatgc gattgagtcc ggtcacattc gtggcgctgg tttcgatgtg   780
tactccaccg agccttgcac tgattctcct ttgttcaagt tgcctcaggt tgttgtgact   840
cctcacttgg gtgcttctac tgaagaggct caggatcgtg cgggtactga cgttgctgat   900
tctgtgctca aggcgctggc tggcgagttc gtggcggatg ctgtgaacgt ttccggtggt   960
cgcgtgggcg aagaggttgc tgtgtggatg gatctggctt aa                      1002

<210> SEQ ID NO 30
<211> LENGTH: 1233
<212> TYPE: DNA
<213> ORGANISM: Artificial Sequence
<220> FEATURE:
<223> OTHER INFORMATION: Modified D-3-phosphoglycerate
      dehydrogenase(G336V), SerA(G336V)

<400> SEQUENCE: 30
atggcaaagg tatcgctgga gaaagacaag attaagtttc tgctggtaga aggcgtgcac     60
caaaaggcgc tggaaagcct tcgtgcagct ggttacacca acatcgaatt tcacaaaggc   120
gcgctggatg atgaacaatt aaaagaatcc atccgcgatg cccacttcat cggcctgcga   180
tcccgtaccc atctgactga agacgtgatc aacgccgcag aaaaactggt cgctattggc   240
tgtttctgta tcggaacaaa ccaggttgat ctggatgcgg cggcaaagcg cgggatcccg   300
gtatttaacg caccgttctc aaatacgcgc tctgttgcgg agctggtgat ggcgaactg   360 ctgctgctat tgcgcggcgt gccggaagcc aatgctaaag cgcaccgtgg cgtgtggaac   420
aaactggcgg cgggttcttt tgaagcgcgc ggcaaaaagc tgggtatcat cggctacggt   480
catattggta cgcaattggg cattctggct gaatcgctgg gaatgtatgt ttactttta   540 gatattgaaa ataaactgcc gctgggcaac gccactcagg tacagcatct ttctgacctg   600
```

```
ctgaatatga gcgatgtggt gagtctgcat gtaccagaga atccgtccac caaaaatatg      660
atgggcgcga aagaaatttc actaatgaag cccggctcgc tgctgattaa tgcttcgcgc      720
ggtactgtgg tggatattcc ggcgctgtgt gatgcgctgg cgagcaaaca tctggcgggg      780
gcggcaatcg acgtattccc gacggaaccg gcgaccaata gcgatccatt tacctctccg      840
ctgtgtgaat tcgacaacgt ccttctgacg ccacacattg gcggttcgac tcaggaagcg      900
caggagaata tcggcctgga agttgcgggt aaattgatca agtattctga caatggctca      960
acgctctctg cggtgaactt cccggaagtc tcgctgccac tgcacgttgg cgtcgtctg      1020 atgcacatcc acgaaaaccg tccgggcgtg ctaactgcgc tgaacaaaat cttcgccgag     1080
cagggcgtca acatcgccgc gcaatatctg caaacttccg cccagatggg ttatgtggtt     1140
attgatattg aagccgacga agacgttgcc gaaaaagcgc tgcaggcaat gaaagctatt     1200
ccgggtacca ttcgcgcccg tctgctgtac taa                                   1233

<210> SEQ ID NO 31
<211> LENGTH: 1233
<212> TYPE: DNA
<213> ORGANISM: Artificial Sequence
<220> FEATURE:
<223> OTHER INFORMATION: Modified serA*(G336V,G337V)

<400> SEQUENCE: 31
atggcaaagg tatcgctgga aaagacaag attaagtttc tgctggtaga aggcgtgcac       60
caaaaggcgc tggaaagcct tcgtgcagct ggttacacca acatcgaatt tcacaaaggc     120
gcgctggatg atgaacaatt aaaagaatcc atccgcgatg cccacttcat cggcctgcga     180
tcccgtaccc atctgactga agacgtgatc aacgccgcag aaaaactggt cgctattggc     240
tgtttctgta tcggaacaaa ccaggttgat ctggatgcgg cggcaaagcg cgggatcccg     300
gtatttaacg caccgttctc aaatacgcgc tctgttgcgg agctggtgat tggcgaactg     360
ctgctgctat tgcgcggcgt gccggaagcc aatgctaaag cgcaccgtgg cgtgtggaac     420
aaactggcgg cgggttcttt tgaagcgcgc ggcaaaaagc tgggtatcat cggctacggt     480
catattggta cgcaattggg cattctggct gaatcgctgg gaatgtatgt ttactttat      540 gatattgaaa ataaactgcc gctgggcaac gccactcagg tacagcatct ttctgacctg     600
ctgaatatga gcgatgtggt gagtctgcat gtaccagaga atccgtccac caaaaatatg     660
atgggcgcga aagaaatttc actaatgaag cccggctcgc tgctgattaa tgcttcgcgc     720
ggtactgtgg tggatattcc ggcgctgtgt gatgcgctgg cgagcaaaca tctggcgggg     780
gcggcaatcg acgtattccc gacggaaccg gcgaccaata gcgatccatt tacctctccg     840
ctgtgtgaat tcgacaacgt ccttctgacg ccacacattg gcggttcgac tcaggaagcg     900
caggagaata tcggcctgga agttgcgggt aaattgatca agtattctga caatggctca     960
acgctctctg cggtgaactt cccggaagtc tcgctgccac tgcacgttgt cgtcgtctg     1020 atgcacatcc acgaaaaccg tccgggcgtg ctaactgcgc tgaacaaaat cttcgccgag    1080
cagggcgtca acatcgccgc gcaatatctg caaacttccg cccagatggg ttatgtggtt    1140
attgatattg aagccgacga agacgttgcc gaaaaagcgc tgcaggcaat gaaagctatt    1200
ccgggtacca ttcgcgcccg tctgctgtac taa                                  1233

<210> SEQ ID NO 32
<211> LENGTH: 1233
<212> TYPE: DNA
```

<213> ORGANISM: Artificial Sequence
<220> FEATURE:
<223> OTHER INFORMATION: Modified serA*(G336V,R338G)

<400> SEQUENCE: 32

```
atggcaaagg tatcgctgga gaaagacaag attaagtttc tgctggtaga aggcgtgcac      60
caaaaggcgc tggaaagcct tcgtgcagct ggttacacca acatcgaatt tcacaaaggc     120
gcgctggatg atgaacaatt aaaagaatcc atccgcgatg cccacttcat cggcctgcga     180
tcccgtaccc atctgactga agacgtgatc aacgccgcag aaaaactggt cgctattggc     240
tgtttctgta tcggaacaaa ccaggttgat ctggatgcgg cggcaaagcg cgggatcccg     300
gtatttaacg caccgttctc aaatacgcgc tctgttgcgg agctggtgat tggcgaactg     360
ctgctgctat tgcgcggcgt gccggaagcc aatgctaaag cgcaccgtgg cgtgtggaac     420
aaactggcgg cgggttcttt tgaagcgcgc ggcaaaaagc tgggtatcat cggctacggt     480
catattggta cgcaattggg cattctggct gaatcgctgg aatgtatgt ttactttat     540
gatattgaaa ataaactgcc gctgggcaac gccactcagg tacagcatct ttctgacctg     600
ctgaatatga gcgatgtggt gagtctgcat gtaccagaga atccgtccac caaaaatatg     660
atgggcgcga agaaatttc actaatgaag cccggctcgc tgctgattaa tgcttcgcgc     720
ggtactgtgg tggatattcc ggcgctgtgt gatgcgctgg cgagcaaaca tctggcgggg     780
gcggcaatcg acgtattccc gacgaaccg gcgaccaata gcgatccatt acctctccg     840
ctgtgtgaat tcgacaacgt ccttctgacg ccacacattg gcggttcgac tcaggaagcg     900
caggagaata tcggcctgga agttgcgggt aaattgatca agtattctga caatggctca     960
acgctctctg cggtgaactt cccggaagtc tcgctgccac tgcacgttgg gggtcgtctg    1020
atgcacatcc acgaaaaccg tccgggcgtg ctaactgcgc tgaacaaaat cttcgccgag    1080
cagggcgtca acatcgccgc gcaatatctg caaacttccg cccagatggg ttatgtggtt    1140
attgatattg aagccgacga agacgttgcc gaaaaagcgc tgcaggcaat gaaagctatt    1200
ccgggtacca ttcgcgcccg tctgctgtac taa                                 1233
```

<210> SEQ ID NO 33
<211> LENGTH: 362
<212> TYPE: PRT
<213> ORGANISM: Escherichia coli
<220> FEATURE:
<221> NAME/KEY: PEPTIDE
<222> LOCATION: (1)..(362)
<223> OTHER INFORMATION: 3-phosphoserine/phosphohydroxythreonine aminotransferase, SerC

<400> SEQUENCE: 33

```
Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
            20                  25                  30

Gly Thr Ser Val Met Glu Val Ser His Arg Gly Lys Glu Phe Ile Gln
        35                  40                  45

Val Ala Glu Glu Ala Glu Lys Asp Phe Arg Asp Leu Leu Asn Val Pro
    50                  55                  60

Ser Asn Tyr Lys Val Leu Phe Cys His Gly Gly Gly Arg Gly Gln Phe
65                  70                  75                  80

Ala Ala Val Pro Leu Asn Ile Leu Gly Asp Lys Thr Thr Ala Asp Tyr
                85                  90                  95
```

Val Asp Ala Gly Tyr Trp Ala Ala Ser Ala Ile Lys Glu Ala Lys Lys
            100                 105                 110

Tyr Cys Thr Pro Asn Val Phe Asp Ala Lys Val Thr Val Asp Gly Leu
        115                 120                 125

Arg Ala Val Lys Pro Met Arg Glu Trp Gln Leu Ser Asp Asn Ala Ala
    130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Ala Ala Asp Phe Ser
                165                 170                 175

Ser Thr Ile Leu Ser Arg Pro Ile Asp Val Ser Arg Tyr Gly Val Ile
            180                 185                 190

Tyr Ala Gly Ala Gln Lys Asn Ile Gly Pro Ala Gly Leu Thr Ile Val
        195                 200                 205

Ile Val Arg Glu Asp Leu Leu Gly Lys Ala Asn Ile Ala Cys Pro Ser
    210                 215                 220

Ile Leu Asp Tyr Ser Ile Leu Asn Asp Asn Gly Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Asn Gly Gly Val Ala Glu Met Asp Lys Ile Asn Gln Gln Lys
            260                 265                 270

Ala Glu Leu Leu Tyr Gly Val Ile Asp Asn Ser Asp Phe Tyr Arg Asn
        275                 280                 285

Asp Val Ala Lys Ala Asn Arg Ser Arg Met Asn Val Pro Phe Gln Leu
    290                 295                 300

Ala Asp Ser Ala Leu Asp Lys Leu Phe Leu Glu Glu Ser Phe Ala Ala
305                 310                 315                 320

Gly Leu His Ala Leu Lys Gly His Arg Val Val Gly Gly Met Arg Ala
                325                 330                 335

Ser Ile Tyr Asn Ala Met Pro Leu Glu Gly Val Lys Ala Leu Thr Asp
            340                 345                 350

Phe Met Val Glu Phe Glu Arg Arg His Gly
        355                 360

<210> SEQ ID NO 34
<211> LENGTH: 1089
<212> TYPE: DNA
<213> ORGANISM: Escherichia coli
<220> FEATURE:
<221> NAME/KEY: gene
<222> LOCATION: (1)..(1089)
<223> OTHER INFORMATION: 3-phosphoserine/phosphohydroxythreonine
      aminotransferase, SerC

<400> SEQUENCE: 34
atggctcaaa tcttcaattt tagttctggt ccggcaatgc taccggcaga ggtgcttaaa        60
caggctcaac aggaactgcg cgactggaac ggtcttggta cgtcggtgat ggaagtgagt       120
caccgtggca agagttcat tcaggttgca gaggaagccg agaaggattt tcgcgatctt        180
cttaatgtcc cctccaacta caaggtatta ttctgccatg cggtggtcg cggtcagttt       240 gctgcggtac cgctgaatat ctcgggtgat aaaaccaccg cagattatgt tgatgccggt       300
tactgggcgg caagtgccat taagaagcg aaaaaatact gcacgcctaa tgtctttgac        360
gccaaagtga ctgttgatgg tctgcgcgcg gttaagccaa tgcgtgaatg caactctct        420 gataatgctg cttatatgca ttattgcccg aatgaaacca tcgatggtat cgccatcgac       480

```
gaaacgccag acttcggcgc agatgtggtg gtcgccgctg acttctcttc aaccattctt    540
tcccgtccga ttgacgtcag ccgttatggt gtaatttacg ctggcgcgca gaaaaatatc    600
ggcccggctg gcctgacaat cgtcatcgtt cgtgaagatt tgctgggcaa agcgaatatc    660
gcgtgtccgt cgattctgga ttattccatc ctcaacgata acggctccat gtttaacacg    720
ccgccgacat ttgcctggta tctatctggt ctggtcttta aatggctgaa agcgaacggc    780
ggtgtagctg aaatggataa aatcaatcag caaaaagcag aactgctata tggggtgatt    840
gataacagcg atttctaccg caatgacgtg gcgaaagcta accgttcgcg gatgaacgtg    900
ccgttccagt tggcggacag tgcgcttgac aaattgttcc ttgaagagtc ttttgctgct    960
ggccttcatg cactgaaagg tcaccgtgtg gtcggcggaa tgcgcgcttc tatttataac   1020
gccatgccgc tggaaggcgt taaagcgctg acagacttca tggttgagtt cgaacgccgt   1080
cacggttaa                                                           1089
```

MICROORGANISM PRODUCING O-PHOSPHOSERINE AND A METHOD FOR PRODUCING O-PHOSPHOSERINE OR L-CYSTEINE USING THE SAME

CROSS-REFERENCES TO RELATED APPLICATIONS

This application is a U.S. national phase application of International PCT Patent Application No. PCT/KR2015/008336, which was filed on Aug. 10, 2015, which claims priority to Korean Patent Application No. 10-2014-0104670, filed Aug. 12, 2014. This application is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_056_00US_ST25.txt. The text file is 62 KB, was created on Jan. 27, 2017, and is being submitted electronically via EFS-Web.

TECHNICAL FIELD

The present invention relates to a microorganism capable of producing O-phosphoserine, and a method of producing O-phosphoserine, cysteine, or a cysteine derivative using the microorganism.

BACKGROUND ART

L-cysteine, an amino acid playing an important role in the metabolism of sulfur in all living organisms, is used not only in the synthesis of biological proteins such as hair keratin, glutathione, biotin, methionine, and other sulfur-containing metabolites, but also as a precursor for biosynthesis of coenzyme A.

Known methods of producing L-cysteine using microorganisms include: 1) a method of biologically converting D,L-ATC to L-cysteine using microorganisms, 2) a method of producing L-cysteine by direct fermentation using E. coli (EP0885962B; Wada M and Takagi H, Appl. Microbiol. Biochem., 73:48-54, 2006), and 3) a method of producing O-phosphoserine ("OPS", hereinafter) by fermentation using microorganisms, and converting OPS into L-cysteine by reacting OPS with a sulfide under the catalytic action of O-phosphoserine sulfhydrylase ("OPSS", hereinafter) (Korean Patent No. 1381048).

In particular, for the production of cysteine by the method 3) at high yield, the precursor, OPS, should be produced in excessive amounts. In this regard, the present inventors have made extensive efforts to discover an appropriate export factor that enables O-phosphoserine produced in an OPS-producing microorganism to be exported from cells smoothly.

DISCLOSURE

Technical Problem

Under these circumstances, the present inventors discovered two novel OPS-producing polypeptides, YhhS and MdtD, and confirmed that OPS can be effectively exported from an OPS-producing microorganism by activating the two polypeptides, thereby completing the present invention.

Technical Solution

It is therefore an object of the present invention to provide an OPS-producing microorganism, wherein the activity of a polypeptide capable of exporting OPS is enhanced compared to its endogenous activity.

Another object of the present invention is to provide a method for producing OPS including; culturing an OPS-producing microorganism in a medium, and separating OPS from the OPS-producing microorganism or its culture.

Still another object of the present invention is to provide uses of the OPS production or export by the polypeptide.

Still another object of the present invention is to provide a method for producing cysteine or its derivative including: a) producing OPS by culturing an OPS-producing microorganism, wherein the activity of a polypeptide capable of exporting OPS is enhanced compared to its endogenous activity, in a medium; and b) reacting the OPS produced in a) or a culture containing the same with a sulfide, in the presence of OPS sulfhydrylase or a microorganism capable of expressing the same.

Advantageous Effects of the Invention

The novel polypeptide with an amino acid sequence of SEQ ID NO: 1 or SEQ ID NO: 2 of the present invention has an excellent OPS-exporting capability. Accordingly, when the novel polypeptide of the present invention is applied to a microorganism capable of producing OPS, it can result in high yield of OPS production, and also can be effectively used for the synthesis of L-cysteine, etc.

DESCRIPTION OF DRAWINGS

FIG. 1 shows a graph illustrating the measurement result of intracellular level of OPS by high performance liquid chromatography (HPLC), after removing all OPS exported from the culture of the recombinant microorganism of the present invention where the functions of YhhS and MdtD proteins were enhanced.

BEST MODE

In an aspect, the present invention provides an OPS-producing microorganism, wherein the activity of a polypeptide, which has an amino acid sequence of SEQ ID NO: 1 or SEQ ID NO: 2 and is capable of exporting O-phosphoserine, is enhanced compared to its endogenous activity.

As used herein, the term "O-phosphoserine" ("OPS", hereinafter) refers to an ester of serine and phosphoric acid that is a component of many proteins. In particular, the OPS is a precursor of L-cysteine and can be converted to cysteine by reacting with a sulfide under the catalytic action of OPS sulfhydrylase (hereinafter described as "OPSS") (Korean Patent No. 1381048). Accordingly, it is an important factor to increase OPS production in cysteine production, and thus it has been required to develop transporters that enable intracellular OPS to be effectively secreted from OPS-producing strains.

As used herein, the term "a polypeptide having the activity of exporting O-phosphoserine" refers to a membrane protein which has the activity of exporting the OPS in a cell to the outside of the cell, and specifically may be a membrane protein derived from E. coli. Two kinds of membrane proteins were identified from *E. coli* where growth inhibition is removed in a condition where an excess amount of OPS is present. Specifically, the thus-identified membrane proteins with OPS-exporting capability are YhhS MFS (major facilitator superfamily) transporter having an amino sequence of SEQ ID NO: 1, and YegB MFS transporter having an amino sequence of SEQ ID NO: 2. In the present invention, the YegB MFS transporter may be interchangeably used with MdtD. The OPS-exporting capability of the protein has not been known until first verified in the present invention.

Additionally, the polypeptide may be an amino acid sequence represented by SEQ ID NO: 1 or SEQ ID NO: 2, and may include, without limitation, membrane proteins having a sequence homology of at least 70% to the above sequences, specifically at least 80%, more specifically at least 90%, and even more specifically at least 95%, as long as they have an OPS-exporting capability, which is substantially the same as or equivalent to that of the polypeptide. Furthermore, it is obvious that polypeptide variants, in which part of the sequence is deleted, modified, substituted, or inserted, should be included in the scope of the present invention, as long as they are amino acid sequences having these homologies and the OPS-exporting capability.

Additionally, the polynucleotide sequence of the polypeptide exhibiting OPS-exporting capability may include polynucleotide sequences encoding the amino acids represented by SEQ ID NO: 1 or SEQ ID NO: 2. Additionally, considering the codons preferred by organisms to express the polypeptide based on the genetic code degeneracy, various modifications may be executed on the coding region within the scope not changing the amino acid sequence of the polypeptide. The polynucleotide sequence may be an amino acid sequence represented by SEQ ID NO: 3 or SEQ ID NO: 4, and may include nucleotide sequences having a sequence homology of at least 70% to these sequences, but is not limited thereto.

As used herein, the term "homology" refers to a degree of identity with a given polypeptide sequence or polynucleotide sequence, and may be indicated in percentage. As used herein, the homologous sequence having the same or similar activity with the given polypeptide sequence or polynucleotide sequence may be indicated in terms of "% homology". The % homology may be confirmed using standard software, i.e., BLAST 2.0, for calculating parameters such as score, identity, and similarity, or by comparing sequences via southern hybridization experiments, and the appropriate hybridization condition to be defined may be determined by a method known to a skilled person in the art (e.g., Sambrook et al., 1989, infra).

In an exemplary embodiment of the present invention, it was confirmed that when the activities of YhhS protein (SEQ ID NO: 1) or MdtD protein (SEQ ID NO: 2) were enhanced in a microorganism capable of producing OPS, the microorganism was shown to have superior OPS-exporting capability to the strain where the RhtB protein was enhanced (Korean Patent Application Publication No. 10-2012-0041115) (a positive control), or the strain where the activities of MFS transporters of EmrD or YcaD were enhanced (an experimental group). The "RhtB" is a membrane protein, encoded by rhtB gene, which can export homoserine/homoserine lactone. Since it was already confirmed that the enhancement of the RhtB activity in an OPS-producing strain increases the OPS-exporting capability in the strain (Korean Patent No. 138104), this was used as a positive control. When the activities of the RhtB protein and the YhhS and MdtD proteins of the present invention were enhanced in an OPS-producing strain, respectively, the RhtB protein and the YhhS and MdtD proteins of the present invention exhibited excellent OPS-exporting capabilities to the RhtB protein. Additionally, the terms "EmrD" and "YcaD" refer to MFS transporter proteins of *E. coli*, and are encoded by emrD gene and ycaD gene, respectively. The EmrD and YcaD, being proteins belonging to MFS transporters as in the YhhS and MdtD proteins, were used as an experimental group to examine whether other proteins belong to the MFS transporter can also exhibit OPS-exporting capabilities. As a result, it was confirmed that EmrD and YcaD proteins, unlike YhhS and MdtD proteins, did not exhibit OPS-exporting capabilities.

Meanwhile, the polypeptide of the present invention has the OPS-exporting capability, and thus, when the activity of the polypeptide is enhanced compared to its endogenous activity in a microorganism having an OPS-producing capability, OPS can be produced effectively.

As used herein, the term "OPS production" not only refers to the production of OPS within a strain, but also to the export of the OPS in a cell to the outside of the cell, for example, to a medium, and specifically, the export of OPS from the inside to the outside of a cell.

As used herein, the term "endogenous activity" refers to an active state of a polypeptide in a microorganism in a natural state, i.e., in a non-modified state.

As used herein, the term "enhancement compared to its endogenous activity" refers to an increased activity of a polypeptide in a microorganism when compared with that possessed in its natural state, and is a concept including rendering the activity of a particular polypeptide in a microorganism which does not possess the activity of the particular polypeptide.

As used herein, the term "enhancement of activity" refers to, although is not particularly limited to, not only the drawing of a higher effect than the original function due to the increase in the activity of the polypeptide itself, but also the increase in the activity of the protein due to the increase in endogenous gene activity, endogenous gene amplification by the internal or external factors, replacement, modification, or mutation of a promoter, etc. Specifically, the enhancement of activity may be performed by methods such as a method of increasing copy number of a gene encoding the polypeptide in a cell, a method of modifying the regulation sequence of a gene encoding the polypeptide, a method of substituting the gene encoding the polypeptide on the chromosome with a mutated gene to increase the activity of the polypeptide, a method of introducing a modification in the gene encoding the polypeptide on the chromosome to enhance the activity of the polypeptide, etc., but is not limited thereto. These methods of enhancing activity may be referenced in the same manner to enhance the activities of other polypeptides of the present invention.

In the above, the increase in gene copy number, although not particularly limited thereto, may be performed in a state operably connected to a vector, or by being inserted into the chromosome within a host cell. Specifically, the method may be executed by introducing a vector, by which a polynucleotide encoding the protein of the present invention is operably connected to a host cell, and can be replicated and function irrespective of a host, into a cell of the host; or introducing a vector, to which the polynucleotide is operably connected, capable of inserting the polynucleotide into the chromosome of the host cell, into the host cell. The insertion of the polynucleotide into the chromosome may be performed using a known method in the art, for example, by homologous recombination. Since the vector of the present invention can be inserted into the chromosome via homologous recombination, a selection marker for confirmation of the insertion into the chromosome may be further included. The selection marker is used for selection of a transformed cell, i.e., in order to confirm whether the target polynucleotide has been inserted, and markers capable of providing selectable phenotypes such as drug resistance, nutrient requirement, resistance to cytotoxic agents, and expression of surface proteins may be used, but are not limited thereto. Under the circumstances where selective agents are treated, only the cells capable of expressing the selection markers can survive or express other phenotypic traits, and thus the transformed cells can be easily selected.

The vector may be a DNA construct including the polynucleotide sequence of the polynucleotide encoding the target protein, which is operably connected to a suitable regulation sequence so that the target protein can be expressed in an appropriate host. The regulation sequence includes a promoter capable of initiating transcription, a random operator sequence for regulation of the transcription, a sequence encoding a suitable mRNA ribosome-binding domain, and a sequence for regulation of transcription and translation. The vector, after being transformed into a suitable host cell, may be replicated or function irrespective of the host genome, or may be integrated into the host genome itself.

The vector used in the present invention may not be particularly limited as long as the vector is replicable in the host cell, and any vector known in the art may be used. Examples of the vector may include natural or recombinant plasmids, cosmids, viruses, and bacteriophages. For example, as a phage vector or cosmid vector, pWE15, M13, λMBL3, λMBL4, λIXII, λASHII, λAPII, λt10, λt11, Charon4A, Charon21A, etc., may be used; and as a plasmid vector, those based on pBR, pUC, pBluescriptII, pGEM, pTZ, pCL, pET, etc., may be used. Specifically, pDZ, pACYC177, pACYC184, pCL, pECCG117, pUC19, pBR322, pMW118, pCC1BAC vectors, etc., may be used.

As used herein, the term "transformation" refers to a process of introducing a vector including a polynucleotide encoding a target protein into a host cell, thereby enabling the expression of the polynucleotide encoded by the protein in the host cell. For the transformed polynucleotide, it does not matter whether it is inserted into the chromosome of a host cell and located therein or located outside the chromosome, as long as it can be expressed in the host cell. Additionally, the polynucleotide includes DNA and RNA which encode the target protein. The polynucleotide may be inserted in any form insofar as it can be introduced into a host cell and expressed therein. For example, the polynucleotide may be introduced into a host cell in the form of an expression cassette, which is a genetic construct including all essential elements required for self-expression, but is not limited thereto. The expression cassette may conventionally include a promoter operably connected to the polynucleotide, a transcription termination signal, a ribosome-binding domain, and a translation termination signal. The expression cassette may be in the form of an expression vector capable of self-replication. Additionally, the polynucleotide may be introduced into a host cell as it is, and operably connected to a sequence essential for its expression in the host cell.

Additionally, as used herein, the term "operably connected" refers to a functional connection between a promoter sequence, which initiates and mediates the transcription of the polynucleotide encoding the target protein of the present invention, and the above gene sequence.

Then, the modification of the expression regulation sequence for increasing the expression of the polynucleotide, although not particularly limited thereto, may be performed by inducing a variation in the polynucleotide sequence via deletion, insertion, conservative substitution, non-conservative substitution, or a combination thereof so as to further enhance the activity of the expression regulation sequence; or by replacing the polynucleotide sequence with a polynucleotide sequence with a stronger activity. The expression regulation sequence, although not particularly limited thereto, may include a promoter, an operator sequence, a sequence encoding a ribosome-binding domain, and a sequence for regulating termination of transcription and translation, etc.

A strong promoter, instead of the original promoter, may be connected to the upper end of the expression unit of the polynucleotide, but is not limited thereto. Examples of the known strong promoters may include cjl promoter (Korean Patent No. 0620092), lac promoter, trp promoter, trc promoter, tac promoter, lambda phage PR promoter, PL promoter, and tet promoter.

Furthermore, the modification of the polynucleotide sequence on the chromosome, although not particularly limited thereto, may be performed by inducing a variation on the expression regulation sequence of the polynucleotide sequence via deletion, insertion, conservative substitution, non-conservative substitution, or a combination thereof so as to further enhance the activity of the polynucleotide sequence; or by replacing the polynucleotide sequence with an enhanced polynucleotide sequence with a stronger activity.

Generally, the introduction and enhancement of the protein activity may increase the activity or concentration of the corresponding protein relative to the activity or concentration of a wild-type protein or in a microorganism strain from at least 1%, 10%, 25%, 50%, 75%, 100%, 150%, 200%, 300%, 400%, or 500%, to a maximum of 1000% or 2000%, but is not limited thereto.

As used herein, the term "OPS-producing microorganism" refers to a prokaryotic or eukaryotic microbial strain capable of producing OPS therein, and specifically a microorganism capable of accumulating OPS therein by genetic engineering.

In an exemplary embodiment of the present invention, the microorganism is not particularly limited but may be any prokaryotic or eukaryotic microorganism that can produce OPS when the activity of the polypeptide of SEQ ID NO: 1 or 2 is enhanced, and specifically a prokaryotic microorganism. Examples of the microorganism may include microbial strains belonging to the genus *Escherichia*, the genus *Erwinia*, the genus *Serratia*, the genus *Providencia*, the genus *Corynebacterium* and the genus *Brevibacterium*. Specifically, the microorganism may be a microorganism of the genus *Escherichia*. More specifically, it may be *E. coli*. Particularly, a microorganism of the *Escherichia* or the genus *Corynebacterium* can produce OPS and L-serine, because it contains SerA, SerC and SerB proteins that are enzymes in the biosynthesis pathway of L-serine (Ahmed Zahoor, Computational and Structural Biotechnology Journal, vol. 3, 2012 October; Wendisch V F et al., Curr Opin Microbiol. 2006 June; 9(3): 268-74; Peters-Wendisch P et al., Appl Environ Microbiol. 2005 November; 71(11): 7139-44).

Additionally, in the OPS-producing microorganism, the activity of phosphoserine phosphatase (SerB) may be further weakened compared to its endogenous activity.

The SerB has an activity of converting OPS to L-serine, and thus the microorganism modified to reduce the SerB activity has the property of accumulating OPS therein, thus being useful for the production of OPS. The SerB may be a protein having an amino acid sequence represented by SEQ ID NO: 17 or SEQ ID NO: 18, but is not limited thereto. Additionally, the SerB may include an amino acid sequence having a sequence identity of 80% or higher, specifically, 90% or higher, more specifically 95% or higher, and even more specifically 99% or higher, as long as it shows the SerB activity, but is not limited thereto. Additionally, the polynucleotide sequence encoding SerB may have a polynucleotide sequence encoding the amino acids represented by SEQ ID NO: 17 or SEQ ID NO: 18.

Considering the codons preferred by organisms to express the polypeptide based on the genetic code degeneracy, various modifications on the polynucleotide may be executed on the coding region within the scope not changing the amino acid sequence of the polypeptide. The polynucleotide sequence may be an amino acid sequence represented by SEQ ID NO: 19 or SEQ ID NO: 20, and may include nucleotide sequences having a sequence homology of 80% to these sequences, and specifically at least 90%, but is not limited thereto.

As used herein, the term "the attenuation compared to its endogenous activity" refers to a reduction of the protein activity when compared with that possessed in its natural state, and also includes when its activity is removed.

The attenuation is a concept referring to a case when the activity of a protein is reduced compared with that originally possessed by the microorganism due to a modification in the protein-encoding gene, etc., a case when the level of overall protein expression is lower than that of the natural type strain of the microorganism due to inhibition of expression or inhibition of translation of the gene encoding the same, or a case when the gene is not expressed at all, and a case when the gene is expressed but exhibits no activity.

The attenuation or inactivation of a protein activity may be achieved by various methods well known in the art. Examples of the methods may include a method of substituting the gene encoding the protein on the chromosome with a gene mutated so that the enzyme activity can be reduced including the case when the protein activity is removed; a method of modifying the expression regulation sequence of the gene encoding the protein; a method of deleting part or the entirety of a gene encoding the protein on the chromosome; a method of introducing an antisense oligonucleotide (e.g., antisense RNA), which inhibits the translation from the mRNA into a protein via a complementary binding to the transcript of the gene on the chromosome; a method of making the attachment of ribosome impossible by forming a secondary structure by artificially adding a Shine-Dalgarno (SD) sequence and its complementary sequence on the front end of the SD sequence of the gene encoding the protein; a method of reverse transcription engineering (RTE), which adds a promoter so as to be reversely transcribed on the 3' terminus of the open reading frame (ORF) of the corresponding sequence, etc., and also include a combination thereof, but are not limited thereto.

Specifically, the method of deleting part or the entirety of a gene encoding the protein may be executed by replacing the polynucleotide encoding the endogenous target protein within the chromosome with a polynucleotide or a marker gene having a partially deleted nucleic acid sequence, using a vector for inserting chromosomes into bacteria. In an exemplary embodiment, the gene may be deleted by homologous recombination. Additionally, as used herein, the term "part", although it may vary depending on the kinds of polynucleotide, may specifically refer to 1 nucleotide to 300 nucleotides, more specifically 1 nucleotide to 100 nucleotides, and even more specifically 1 nucleotide to 50 nucleotides, but is not limited thereto.

Additionally, the method of modifying the expression regulation sequence may be performed by inducing a variation in the expression regulation sequence via deletion, insertion, conservative substitution, non-conservative substitution, or a combination thereof so as to further weaken the activity of the expression regulation sequence; or by replacing the sequence with a nucleic acid sequence having a weaker activity. The expression regulation sequence includes a promoter, an operator sequence, a sequence encoding ribosome-binding domain, and a sequence for regulating transcription and translation.

Additionally, the method of modifying the gene sequence may be performed by inducing a variation in the gene sequence via deletion, insertion, conservative substitution, non-conservative substitution, or a combination thereof so as to further weaken the activity of the protein; or by replacing the sequence with a gene sequence improved to have a weaker activity or a gene sequence improved to have no activity at all.

Additionally, the OPS-producing microorganism may be one in which the activities of phosphoglycerate dehydrogenase (SerA) or phosphoserine aminotransferase (Serf) are further enhanced compared to their endogenous activities.

The SerA is a protein capable of converting 3-phosphoglycerate into 3-phospho-hydroxypyruvate, and for SerA, a wild-type or a variant, where the feedback on serine is removed, may be used. Additionally, the SerC is a protein capable of converting 3-phospho-hydroxypyruvate to OPS. Accordingly, any microorganism with enhanced SerA and/or SerC activities may be effectively used as an OPS-producing microorganism.

The SerA may have an amino acid sequence selected from the group consisting of SEQ ID NOS: 21 to 26, although is not limited thereto. The SEQ ID NO: 21 is a sequence of wild-type SerA, and SEQ ID NOS: 22 to 26 are sequences of variants where the feedback on serine is removed. Additionally, those amino acid sequences which have at least 80% sequence identity to the above amino acids, specifically at least 90%, more specifically at least 95%, and even more specifically at least 99% may be included as long as they exhibit the activities of the wild-type SerA or SerA variants where the feedback on serine is removed, but are not limited thereto. The variants where the feedback is removed represent those proteins in which a modification is introduced on the SerA-encoding gene by insertion, substitution, etc., thereby enabling maintaining of the activity from the feedback inhibition by serine or glycine, or having enhanced activities thereof, and those variants where the feedback is removed are already well known (Grant G A et al., J. Biol. Chem., 39: 5357-5361, 1999; Grant G A et al., Biochem., 39: 7316-7319, 2000; Grant G A et al., J. Biol. Chem., 276: 17844-17850, 2001; Peters-Wendisch P et al., Appl. Microbiol. Biotechnol., 60: 437-441, 2002; EP Pat. No. EP0943687B).

Additionally, the polynucleotide sequence encoding the wild-type SerA or the variants, where the feedback on serine is removed, may be a polynucleotide sequence encoding any one amino acid sequence represented by SEQ ID NOS: 21 to 26, but is not limited thereto. Due to the genetic code degeneracy or considering the codons preferred by organisms to express the polypeptide, various modifications on the polynucleotide may be executed on the coding region within the scope not changing the amino acid sequence of the polypeptide. The polynucleotide sequence may be, for example, any one of polynucleotide sequences represented by SEQ ID NOS: 27 to 32, and may have a nucleotide sequence having a homology of at least 80% to the polynucleotide sequences, and specifically at least 90%, but is not limited thereto.

The SerC may be a protein having an amino acid sequence which is, for example, represented by SEQ ID NO: 33, but is not limited thereto. Additionally, the amino acid sequence, as long as it exhibits the activity of SerC, may also include amino acid sequences which have a sequence identity of at least 80% to the above amino acid sequence, specifically at least 90%, more specifically at least 95%, and even more specifically at least 99%, but is not limited thereto.

Additionally, the polynucleotide sequence encoding the SerC may be the polynucleotide sequence encoding the amino acid represented by SEQ ID NO: 33. Due to the genetic code degeneracy or considering the codons preferred by organisms to express the polypeptide, various modifications on the polynucleotide may be executed on the coding region within the scope not changing the amino acid sequence of the polypeptide. The polynucleotide sequence may be, for example, one represented by SEQ ID NO: 34, and may have a nucleotide sequence having a homology of at least 80% to the polynucleotide sequences, and specifically at least 90%, but is not limited thereto.

Additionally, the microorganism may be one in which the capability of introducing or decomposing OPS into a cell is further weakened.

Regarding the contents on the OPS-producing microorganism, the disclosure in Korean Patent No. 1381048 or U.S. Patent Application Publication No. 2012-0190081 may be used as references of the present invention, in addition to those described above.

In another aspect, the present invention provides a method of producing OPS, including culturing a microorganism capable of producing O-phosphoserine in which an activity of a polypeptide, which has an amino acid sequence of SEQ ID NO: 1 or SEQ ID NO: 2 and is capable of exporting O-phosphoserine, is enhanced, in a medium; and separating O-phosphoserine from the microorganism capable of producing O-phosphoserine, or the medium for the same.

As used herein, the term "culturing" refers to growing the microorganism in an appropriately adjusted environment. The culture process may be performed according to the appropriate medium and conditions for culture known in the art. The culture process may be easily adjusted for use by one of ordinary skill in the art according to the strain to be selected. Specifically, the culture may be a batch culture, a continuous culture, and a fetch culture, but is not limited thereto.

In culturing the recombinant microorganism having reduced SerB activity compared to its endogenous activity, the medium may further contain glycine or serine, because the serine requirement of the recombinant microorganism is induced. Glycine may be provided in the form of purified glycine, a glycine-containing yeast extract, or tryptone. The concentration of glycine in the medium is generally 0.1 g/L to 10 g/L, and specifically 0.5 g/L to 3 g/L. Additionally, serine may be provided in the form of purified serine, a serine-containing yeast extract, or tryptone. The concentration of serine in the medium is generally 0.1 g/L to 5 g/L, and specifically 0.1 g/L to 1 g/L.

Examples of the carbon source to be contained in the medium may include carbohydrates and saccharides such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These carbon sources may be used alone or in combination, but are not limited thereto. Examples of the nitrogen source to be contained in the medium may include organic nitrogen sources such as peptone, yeast extract, gravy, malt extract, corn steep liquor (CSL), and bean flour; and inorganic nitrogen sources such as urea, ammonium sulfate, ammonium chloride, ammonium phosphate, ammonium carbonate, and ammonium nitrate. These nitrogen sources may be used alone or in combination, but are not limited thereto. As a phosphorous source, the culture media may further include potassium dihydrogen phosphate, dipotassium hydrogen phosphate, and corresponding sodium-containing salts, but are not limited thereto. The culture media may include metals such as magnesium sulfate and iron sulfate. Additionally, amino acids, vitamins and appropriate precursors may be included. These culture media or precursors may be added to the culture in the form of a batch culture or continuous culture, but are not limited thereto.

Additionally, the pH of the culture may be adjusted by adding a compound such as ammonium hydroxide, potassium hydroxide, ammonia, phosphoric acid, and sulfuric acid during cultivation in an appropriate manner. Additionally, bubble formation may be prevented during the cultivation using an antifoaming agent such as fatty acid polyglycol ester. Additionally, an oxygen gas or a gas containing an oxygen gas may be added to a culture in order to maintain aerobic conditions in a culture liquid; no air may be added to maintain anaerobic conditions or microaerobic conditions; or nitrogen gas, hydrogen gas, or carbon dioxide may be injected. The culture temperature may be from 27° C. to 37° C., and specifically from 30° C. to 35° C. The cultivation may be continued until the production of desired material can be obtained, and specifically for 10 hours to 100 hours.

In the present invention, the OPS produced during the cultivation may be further separated and purified. The intended OPS may be recovered from the culture using an appropriate method known in the art, according to the culture method, e.g., a batch culture, a continuous culture, and a fetch culture, but is not limited thereto.

In another aspect, the present invention provides uses of OPS production and OPS export by the polypeptide, which has the amino acid sequence of SEQ ID NO: 1 or SEQ ID NO: 2.

In still another aspect, the present invention provides a method for producing cysteine or a derivative thereof including a) producing O-phosphoserine (OPS) by culturing a microorganism, in which an activity of a polypeptide which has an amino acid sequence of SEQ ID NO: 1 or SEQ ID NO: 2 and is capable of exporting O-phosphoserine is enhanced compared to its endogenous activity, in a medium; and b) reacting the O-phosphoserine (OPS) produced in a) or a culture containing the same with a sulfide in the presence of O-phosphoserine sulfhydrylase (OPSS) or a microorganism capable of expressing the same.

As used herein, the term "O-phosphoserine sulfhydrylase" ("OPSS", hereinafter) refers to a polypeptide that catalyzes a reaction in which a thiol (SH) group is provided to OPS to convert OPS into cysteine. The enzyme was first found in *Aeropyrum pernix*, *Mycobacterium tuberculosis*, *Mycobacterium smegmatics*, and *Trichomonas vaginalis* (Mino K and Ishikawa K, FEBS Letters, 551: 133-138, 2003; Burns K E et al., J. Am. Chem. Soc., 127: 11602-11603, 2005). In addition, the scope of OPSS includes not only wild-type OPSS protein, but also variants that include deletion, substitution, or addition in part of the polynucleotide sequence encoding the OPSS, which show activity that is equal to or higher than the biological activity of wild-type OPSS protein, for example, and includes the OPSS proteins disclosed in Korean Patent Nos. 1381048 and 1208267 and their variants.

The sulfide to be used in the present invention may be any sulfide provided not only in a solid form generally used in the art, but also in a liquid or gas form due to the difference in pH, pressure, and solubility, and thus can be converted to a thiol (SH) group in the form of, for example, sulfide ($S^{2-}$) or thiosulfate ($S_2O_3^{2-}$). Specifically, the sulfide to be used in the present invention may be $Na_2S$, NaSH, $H_2S$, $(NH_4)_2S$, or $Na_2S_2O_3$, which can provide a thiol group to OPS. In the reaction, a single thiol group is supplied to a single reactive OPS group to produce a single cysteine or a derivative thereof. In this reaction, a sulfide is specifically added in an amount of 0.1 mol to 3 mol, and specifically 1 mol to 2 mol per 1 mol of OPS.

In addition, the method of the present invention further includes separating and purifying the cysteine produced in reaction of step b). Herein, the desired cysteine can be recovered by isolating and purifying it from the reaction solution by a suitable reaction known in the art.

Additionally, the present invention relates to a high-yield production of OPS obtained by enhancing the activity of the polypeptide of SEQ ID NO: 1 or SEQ ID NO: 2 in an OPS-producing microorganism, followed by reacting the thus-produced OPS with OPSS, thereby effectively producing cysteine. The thus-prepared cysteine may be synthesized in various kinds of cysteine derivatives via a chemical synthesis reaction known in the art by modifying a hydrogen atom or a particular atom group.

As used herein, the term "derivatives" refers to similar compounds obtained by chemically modifying a portion of any compound. Usually, the term refers to compounds in which a hydrogen atom or an atom group is substituted with another hydrogen atom or atom group.

As used herein, the term "cysteine derivatives" refers to compounds in which a hydrogen atom or atom group in cysteine is substituted with another atom or atom group. For example, the cysteine derivatives may have a form in which the nitrogen atom of the amine group (—$NH_2$) or the sulfur atom of the thiol group (—SH) in cysteine has another atom or atom group attached thereto. Examples of cysteine derivatives include N-acetylcysteine (NAC), S-carboxymethylcysteine (SCMC), Boc-Cys(Me)-OH, (R)—S-(2-amino-2-carboxyethyl)-L-homocysteine, (R)-2-amino-3-sulfopropionic acid, D-2-amino-4-(ethylthio)butyric acid, 3-sulfino-L-alanine, Fmoc-Cys(Boc-methyl)-OH, seleno-L-cysteine, S-(2-thiazolyl)-L-cysteine, S-(2-thienyl)-L-cysteine, S-(4-tolyl)-L-cysteine, but are not limited thereto. Cysteine can be easily synthesized into N-acetylcysteine (NAC) by reaction with an acetylation agent, and in basic conditions, it can be synthesized into S-carboxymethylcysteine (SCMC) by a reaction with a haloacetic acid. These cysteine derivatives are used mainly as pharmaceutical materials for antitussive agents, cough-relieving agents, and therapeutic agents for bronchitis, bronchial asthma, laryngopharyngitis, etc.

MODE FOR INVENTION

Hereinafter, the present invention will be described in more detail with reference to the following Examples. However, these Examples are for illustrative purposes only, and the invention is not intended to be limited by these Examples.

Example 1

Identification of YhhS MFS Transporter and YegB MFS Transporter

In order to identify *Escherichia coli* membrane proteins involved in the export of OPS, a genomic DNA library of *Escherichia coli* K12_W3110 (ATCC27325) was screened. Specifically, to set up the conditions in which the growth of *E. coli* is inhibited by OPS, a platform strain producing OPS was constructed. The platform strain for screening was a recombinant microorganism modified to reduce the activity of endogenous phosphoserine phosphatase (SerB) in the wild-type *E. coli* strain W3110, and was designated as "KCCM11212P" (also called "CA07-0012"; Korean Patent No. 10-1381048; US Patent Application Publication No. 2012-0190081). Using the OPS-producing strain KCCM11212P, optimal screening conditions showing growth inhibition were established by culturing the KCCM11212P, which is an OPS-producing strain, in a medium containing OPS.

Then, the genomic library plasmids of W3110 were transformed into CA07-0012 by electroporation (van der Rest et al. 1999), and colonies showing the removal of growth inhibition under medium conditions containing an excessive amount of OPS were selected. Plasmids were obtained from the selected colonies, and the nucleotide sequences thereof were analyzed by a sequencing technique. As a result, two *E. coli* membrane proteins involved in removing growth inhibition under medium conditions containing an excessive amount of OPS were identified.

The two *E. coli* membrane proteins were identified to be yhhS and mdtD, which encode YhhS major facilitator superfamily (MFS) transporter (an amino acid sequence of SEQ ID NO: 1 and a nucleotide sequence of SEQ ID NO: 3) and YegB MFS transporter (an amino acid sequence of SEQ ID NO: 2 and a nucleotide sequence of SEQ ID NO: 4), respectively (Pao S S, Paulsen I T, Saier M H (1998). "Major facilitator superfamily." Microbiol Mol Biol Rev 1998; 62(1); 1-34. PMID: 9529885).

Example 2

Construction of yhhS- and mdtD-overexpressing Vectors

In order to examine whether OPS-exporting capability is enhanced when the YhhS MFS transporter and YegB MFS transporter, which are involved in removing growth inhibition by OPS, are enhanced in OPS-producing strains, vectors that overexpress each of the genes were constructed. Additionally, since the present inventors confirmed that the concentration of OPS increased when the homoserine/homoserine lactone transporter RhtB was enhanced in the OPS-producing strain (Korean Patent No. 138104), the RhtB-enhanced strain was used as a positive control. In addition, the multidrug efflux transporters EmrD and YcaD MFS belonging to the major facilitator superfamily (MFS), to which MacB belongs, were also evaluated. In the same manner as in YhhS and MdtD, multidrug efflux transporter EmrD and YcaD MFS transporter, which are *E. coli* membrane proteins belonging to the major facilitator superfamily (MFS), were also evaluated. In this Example, fragments of the gene yhhS (SEQ ID NO: 3, Accession Numbers: b3473) encoding YhhS MFS transporter and fragments of the gene mdtD (SEQ ID NO: 4, Accession Numbers: b2077) encoding YegB MFS transporter were obtained by PCR using the genomic DNA of W3110 as a template.

The primer sequences used for constructing overexpression vectors for each of genes for the membrane proteins are shown in Table 1 below.

TABLE 1

| Gene | Primer (5'→3') | SEQ ID NO | Vector |
|---|---|---|---|
| yhhS | GATATCATGCCCGAACCCGTAGC | 5 | pCL-PrhtB-yhhS |
| | AAGCTTTTAAGATGATGAGGCGGCCT | 6 | |
| mdtD | GATATCATGACAGATCTTCCCGACAGC | 7 | pCL-PrhtB-mdtD |
| | AAGCTTTCATTGCGCGCTCCTTT | 8 | |
| rhtB | GATATCATGACCTTAGAATGGTGG | 9 | pCL-PrhtB-rhtB |
| | AAGCTTTCACGCATGCCTCGCCGA | 10 | |
| emrD | GATATCATGAAAAGGCAAAGAAACGTCAA | 11 | pCL-PrhtB-emrD |
| | AAGCTTTTAAACGGGCTGCCCCT | 12 | |
| ycaD | GATATCATGTCCACGTATACCCAGCCTG | 13 | pCL-PrhtB-ycaD |
| | AAGCTTTTACACGTGAGCAACGGGTTT | 14 | |
| pCL-1920 | AAGCTTCGGGCCTCTTCGCTATTACGC | 15 | pCL-PrhtB |
| | AAGCTTAGGCTTACCCGTCTTACTGTC | 16 | |

Specifically, a PCR reaction for yhhS was performed using the primers of SEQ ID NOS: 5 and 6, whereas a PCR reaction for mdtD was performed using the primers of SEQ ID NOS: 7 and 8. The primers used in the PCR reactions were constructed based on the information of the K12 W3110 gene (GenBank Accession Number AP 003471) deposited in the NIH GenBank and surrounding nucleotide sequences.

Additionally, the fragments of rhtB, emrD, and ycaD genes were amplified via PCT reactions using the respective primer pairs shown in Table 1 below.

Each of the amplified gene fragments was treated with the restriction enzymes EcoRV and HindIII, and cloned into the EcoRV and HindIII restriction enzyme sites of the pCL-PrhtB vector, which includes the promoter (PrhtB) of E. coli rhtB gene inserted into a pCL1920 vector (GenBank No AB236930), thereby constructing pCL-PrhtB-rhtB, pCL-PrhtB-yhhS, pCL-PrhtB-mdtD, pCL-PrhtB-emrD, and pCL-PrhtB-ycaD, respectively.

Example 3

Construction of a Strain with Enhanced YhhS MFS Transporter and YegB MFS Transporter and Evaluation of OPS-producing Capability Example 3-1

Construction of a Strain with Enhanced YhhS MFS Transporter and YegB MFS Transporter Using CA07-0012 and Evaluation of OPS-producing Capability Each of the five kinds of plasmids constructed in Example 2 was introduced into the OPS-producing strain CA07-0012, and then the OPS production capabilities of the resulting strains were evaluated.

Specifically, each of the strains was plated on an LB solid medium and cultured overnight in an incubator at 33° C. Each of the strains cultured overnight on the LB solid medium was inoculated into a 25 mL titer medium shown in Table 2 below, and then incubated in an incubator at 34.5° C. and 200 rpm for 40 hours. The results are shown in Table 3.

TABLE 2

| Composition | Conc. (per 1 L) |
|---|---|
| Glucose | 50 g |
| $KH_2PO_4$ | 6 g |
| $(NH_4)_2SO_4$ | 17 g |
| $MgSO_4 \cdot 7H_2O$ | 1 g |
| $FeSO_4 \cdot 7H_2O$ | 5 mg |
| $MnSO_4 \cdot 4H_2O$ | 10 mg |
| L-Glycine | 2.5 g |
| Yeast extract | 3 g |
| Calcium carbonate | 30 g |
| pH | 6.8 |

TABLE 3

| Strain | OD 562 nm | Glucose consumption (g/L) | O-phosphoserine (g/L) |
|---|---|---|---|
| CA07-0012 | 35 | 32 | 1.1 |
| CA07-0012/pCL-PrhtB-rhtB | 40 | 35 | 1.3 |
| CA07-0012/pCL-PrhtB-yhhS | 37 | 34 | 2.1 |
| CA07-0012/pCL-PrhtB-mdtD | 41 | 32 | 1.8 |
| CA07-0012/pCL-PrhtB-emrD | 38 | 34 | 1.2 |
| CA07-0012/pCL-PrhtB-ycaD | 37 | 33 | 0.9 |

As shown in Table 3 above, among the cases where the E. coli membrane protein genes were further introduced to the E. coli CA07-0012 strain, respectively, the strains having enhanced rhtB, emrD, or ycaD showed significant increases in OPS production, compared to the CA07-0012 strain, and in particular, the strains having enhanced YhhS and MdtD showed an at least 150% increase in OPS concentration. On the contrary, the strains having enhanced EmrD and YcaD, which were used as experimental group, failed to show any increase in OPS concentration.

The strain designated as "CA07-0012/pCL-PrhtB-yhhS" was named as "Escherichia coli CA07-0266 (CA07-0266)" and deposited with the Korean Culture Center of Microorganisms, recognized as an international depositary authority under the Budapest Treaty, on Dec. 9, 2013 under the Accession Number KCCM11495P.

Additionally, the strain designated as "CA07-0012/pCL-PrhtB-mdtD" was named as "Escherichia coli CA07-0267 (CA07-0267)" and deposited with the Korean Culture Center of Microorganisms, recognized as an international depositary authority under the Budapest Treaty, on Dec. 9, 2013 under the Accession Number KCCM11496P.

Example 3-2

Construction of a Strain with Enhanced YhhS MFS Transporter and YegB MFS Transporter Using a Strain with Enhanced SerA and SerC and Evaluation of OPS-producing Capability Additionally, the effects of the E. coli membrane protein genes were examined using the OPS-producing strain, CA07-0022/pCL-Prmf-SerA*(G336V)-(RBS)SerC (Korean Patent Application Publication No. 10-2012-004111), in which the activities of D-3-phosphoglycerate dehydrogenase (SerA) and 3-phosphoserine aminotransferase (SerC) as OPS biosynthesis routes were enhanced. The results are shown in Table 4 below.

TABLE 4

| Strain | OD 562 nm | Glucose consumption (g/L) | O-phosphoserine (g/L) |
|---|---|---|---|
| CA07-0022/pCL-Prmf-SerA*(G336V)-(RBS)SerC | 30 | 27 | 2.4 |
| CA07-0022/pCL-Prmf-SerA*(G336V)-(RBS)SerC-PrhtB-rhtB | 32 | 28 | 2.8 |
| CA07-0022/pCL-Prmf-SerA*(G336V)-(RBS)SerC-PrhtB-yhhS | 28 | 26 | 4.0 |
| CA07-0022/pCL-Prmf-SerA*(G336V)-(RBS)SerC-PrhtB-mdtD | 27 | 27 | 3.5 |
| CA07-0022/pCL-Prmf-SerA*(G336V)-(RBS)SerC-PrhtB-emrD | 33 | 29 | 2.3 |
| CA07-0022/pCL-Prmf-SerA*(G336V)-(RBS)SerC-PrhtB-ycaD | 34 | 28 | 1.9 |

As shown in Table 4 above, it was confirmed again that, among the strains where the *E. coli* membrane protein genes were further introduced to the CA07-0022/pCL-Prmf-SerA*(G336V)-(RBS)SerC strain, the strains having enhanced YhhS and MdtD of the present invention and the strain having enhanced RhtB (positive control) showed increases in OPS production, compared to the *E. coli*-derived CA07-0012 strain. In particular, the strains having enhanced YhhS and MdtD of the present invention showed an at least 145% increase in OPS concentration, similarly to the results shown in Table 3 above. On the contrary, the strains having enhanced ErmD and YcaD showed a decrease in OPS concentration, relative to that of the control group.

Example 3-3

Construction of a Strain with Enhanced YhhS MFS Transporter and YegB MFS Transporter According to Promoter Strength and Evaluation of OPS-producing Capability Additionally, in order to examine whether the enhancement of promoter strength can increase the export capability, the membrane proteins YhhS and MdtD with increased OPS concentration were compared to the control group, by further introducing yhhS and mdtD genes into CA07-0022/pCL-Prmf-SerA*(G336V)-(RBS)SerC, using a trc promoter (Ptrc), which is a stronger promoter than the rhtB promoter (PrhtB).

Each of the fragments of yhhS and mdtD genes was treated with the restriction enzymes EcoRV and HindIII, and cloned into the EcoRV and HindIII restriction enzyme sites of the pCL-Ptrc-GFP vector, which includes the trc promoter inserted into apCL1920 vector, thereby constructing pCL-Ptrc-yhhS and pCL-Ptrc-mdtD, respectively. Then, PCR reactions were performed using each plasmid as a template along with primer pairs of SEQ ID NO: 15 and SEQ ID NO: 16, and the resultants were treated with HindIII and then cloned into the HindIII restriction site of pCL-Prmf-SerA*(G336V)-(RBS)SerC.

TABLE 5

| Strain | OD 562 nm | Glucose consumption (g/L) | O-phosphoserine (g/L) |
|---|---|---|---|
| CA07-0022/pCL-Prmf-SerA*(G336V)-(RBS)SerC | 31 | 30 | 2.7 |
| CA07-0022/pCL-Prmf-SerA*(G336V)-(RBS)SerC-Ptrc-yhhS | 28 | 33 | 5.5 |
| CA07-0022/pCL-Prmf-SerA*(G336V)-(RBS)SerC-Ptrc-mdtD | 29 | 31 | 4.3 |

As a result, as shown in Table 5 above, when the expression of membrane proteins of *E. coli* was increased by enhancing the promoter, there was an at least 150% increase in yield compared to the control group, and an at least 120% increase compared to when the rhtB promoter was used.

Example 3-4

Construction of a Strain with Enhanced YhhS MFS Transporter and YegB MFS Transporter According to Promoter Strength on the Chromosome and Evaluation of OPS-producing Capability Additionally, in order to examine whether replacement of the promoters for yhhS and mdtD genes with stronger promoters on the chromosome can enhance export capability, the OPS production capability was evaluated by constructing a strain, where the self-promoter was replaced with cj1 promoter (Korean Patent No. 0620092). The introduction of the cj1 promoter into the *E. coli* chromosome was executed by a conventional method as described below. For the replacement of self-promoters of yhhS and mdtD on the chromosome, the constructed recombinant vector was transformed into an OPS-producing strain, CA07-0022/pCL-Prmf-SerA*(G336V)-(RBS)SerC (Korean Patent No. 138104), and the above promoter sequence on the vector and the self-promoter sequences were replaced via homologous recombination, and thereby the cj1 promoter sequence was inserted into the chromosome.

Each strain was plated on an LB solid medium and cultured overnight in an incubator at 33° C. Each of the strains cultured overnight on the LB solid medium was inoculated into a 25 mL titer medium shown in Table 2 above, and then incubated in an incubator at 34.5° C. and 200 rpm for 40 hours. The results are shown in Table 6 below.

TABLE 6

| Strain | OD 562 nm | Glucose consumption (g/L) | O-phosphoserine (g/L) |
|---|---|---|---|
| CA07-0022/pCL-Prmf-SerA*(G336V)-(RBS)SerC | 30 | 29 | 2.7 |
| CA07-0022::Pcj1 yhhs/pCL-Prmf-SerA*(G336V)-(RBS)SerC | 28 | 30 | 3.5 |
| CA07-0022::Pcj1 mdtD/pCL-Prmf-SerA*(G336V)-(RBS)SerC | 29 | 31 | 3.2 |

As shown in Table 6 above, when the expression of each membrane protein on the chromosome was increased, the yield relative to that of the control group was increased by up to 130%.

Example 4

Confirmation of OPS-exporting Function of YhhS MFS Transporter and YegB MFS Transporter Among the flask samples, in which OPS production was confirmed in Example 3, after all OPS exported in the medium was removed using CA07-0022/pCL-Prmf-SerA*(G336V)-(RBS)SerC, which is a negative control where the membrane proteins were not enhanced, and samples CA07-0022/pCL-Prmf-SerA*(G336V)-(RBS)SerC-Ptrc-yhhS and CA07-0022/pCL-Prmf-SerA*(G336V)-(RBS)SerC-Ptrc-mdtD, in which the membrane proteins YhhS and MdtD were enhanced, only the cells were collected, and the cells were crushed. The OPS concentration inside the cell was measured by high performance liquid chromatography (HPLC), and the results are shown in FIG. 1.

As a result, as shown in FIG. 1, the strains with enhanced YhhS and MdtD of the present invention showed a decrease in intracellular OPS concentration by 30% to 40%, compared to that of the control group, thus confirming that Yhhs and MdtD proteins play a role in exporting OPS to the outside of the cell. Accordingly, it was confirmed that the enhancement of Yhhs and MdtD proteins can smoothly export OPS in the cell to the outside, thereby enhancing the OPS-producing capability.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents and other embodiments that may be included within the spirit and scope of the present invention as defined by the appended claims.

---

The invention claimed is:

1. A microorganism capable of producing O-phosphoserine (OPS), in which an OPS exporting activity of a polypeptide, which has the amino acid sequence of SEQ ID NO: 1 or SEQ ID NO: 2 and is capable of exporting O-phosphoserine, is enhanced compared to its endogenous activity; and
an activity of phosphoserine phosphatase (SerB) is weakened compared to its endogenous activity.

2. The microorganism of claim 1, in which an activity of phosphoglycerate dehydrogenase (SerA) or phosphoserine aminotransferase (SerC) is enhanced compared to its endogenous activity.

3. The microorganism of claim 1, wherein the microorganism capable of producing O-phosphoserine is *Escherichia coli*.

4. A method for producing O-phosphoserine (OPS), comprising:
culturing a microorganism capable of producing O-phosphoserine, in which an OPS exporting activity of a polypeptide which has the amino acid sequence of SEQ ID NO: 1 or SEQ ID NO: 2 and is capable of exporting O-phosphoserine is enhanced compared to its endogenous activity, in a medium; and
separating O-phosphoserine from the microorganism capable of producing O-phosphoserine, or the medium for the same.

5. The method of claim 4, wherein, in the microorganism capable of producing O-phosphoserine, an activity of phosphoserine phosphatase (SerB) is weakened compared to its endogenous activity.

6. The method of claim 4, wherein, in the microorganism capable of producing O-phosphoserine, an activity of phosphoglycerate dehydrogenase (SerA) or phosphoserine aminotransferase (SerC) is enhanced compared to its endogenous activity.

7. The method of claim 4, wherein the microorganism capable of producing 0-phosphoserine is *Escherichia coli*.

8. A method for producing cysteine or a derivative thereof, comprising:
a) producing O-phosphoserine (OPS) by culturing a microorganism capable of producing O-phosphoserine (OPS), in which an OPS exporting activity of a polypeptide, which has the amino acid sequence of SEQ ID NO: 1 or SEQ ID NO: 2 and is capable of exporting O-phosphoserine, is enhanced compared to its endogenous activity in a medium; and
b) reacting the O-phosphoserine (OPS) produced in a) or a culture containing the same with a sulfide, in the presence of O-phosphoserine sulfhydrylase (OPSS) or a microorganism capable of expressing the same.

9. A method for producing cysteine or a derivative thereof, comprising:
a) producing O-phosphoserine (OPS) by culturing the microorganism according to claim 1 in a medium; and
b) reacting the O-phosphoserine (OPS) produced in a) or a culture containing the same with a sulfide, in the presence of O-phosphoserine sulfhydrylase (OPSS) or a microorganism capable of expressing the same.

10. The method of claim 9, wherein the sulfide is at least one selected from the group consisting of $Na_2S$, NaSH, $(NH_4)_2S$, $H_2S$, and $Na_2S_2O_3$.

11. A method for producing cysteine or a derivative thereof, comprising:
a) producing O-phosphoserine (OPS) by culturing the microorganism according to claim 2 in a medium; and
b) reacting the O-phosphoserine (OPS) produced in a) or a culture containing the same with a sulfide, in the presence of O-phosphoserine sulfhydrylase (OPSS) or a microorganism capable of expressing the same.

12. The method of claim 11, wherein the sulfide is at least one selected from the group consisting of $Na_2S$, NaSH, $(NH_4)_2S$, $H_2S$, and $Na_2S_2O_3$.

13. A method for producing cysteine or a derivative thereof, comprising:
a) producing O-phosphoserine (OPS) by culturing the microorganism according to claim 3 in a medium; and
b) reacting the O-phosphoserine (OPS) produced in a) or a culture containing the same with a sulfide, in the presence of O-phosphoserine sulfhydrylase (OPSS) or a microorganism capable of expressing the same.

14. The method of claim 13, wherein the sulfide is at least one selected from the group consisting of $Na_2S$, NaSH, $(NH_4)_2S$, $H_2S$, and $Na_2S_2O_3$.

* * * * *